(12) United States Patent  (10) Patent No.: US 8,750,991 B2
Lisogurski et al.  (45) Date of Patent: Jun. 10, 2014

(54) MONITORING PHYSIOLOGICAL SIGNALS DURING EXTERNAL ELECTRICAL STIMULATION

(75) Inventors: Daniel M. Lisogurski, Medford, MA (US); Frederick J. Geheb, Danvers, MA (US); Michael R. Dupelle, N. Attleboro, MA (US); Gary A. Freeman, Newton Center, MA (US); Martin E. Bures, Arlington, MA (US); Gideon D. H. Butler, Portsmouth, NH (US); David N. Craige, III, Attleboro, MA (US); Marc Cordaro, Sudbury, MA (US); Deborah T. Jones, Dartmouth, MA (US); Michael Lopin, Newton, MA (US); Michael Parascandola, Londonderry, NH (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 13/450,563

(22) Filed: Apr. 19, 2012

(65) Prior Publication Data

US 2012/0203296 A1  Aug. 9, 2012

Related U.S. Application Data

(62) Division of application No. 11/055,572, filed on Feb. 10, 2005, now Pat. No. 8,185,199.

(51) Int. Cl.
*A61N 1/00* (2006.01)
(52) U.S. Cl.
USPC .............................. 607/9; 600/508
(58) Field of Classification Search
USPC .............................................................. 607/9
See application file for complete search history.

(56) References Cited

U.S. PATENT DOCUMENTS

| 4,112,930 A | 9/1978 | Feldman et al. |
| 4,170,227 A | 10/1979 | Feldman et al. |
| 4,263,919 A | 4/1981 | Levin |
| 4,955,381 A | 9/1990 | Way et al. |
| 4,957,109 A | 9/1990 | Groeger et al. |
| 5,080,099 A | 1/1992 | Way et al. |
| 5,184,620 A | 2/1993 | Cudahy et al. |
| 5,330,512 A | 7/1994 | Hauck et al. |
| 5,466,256 A | 11/1995 | McAdams et al. |
| 5,711,304 A | 1/1998 | Dower |
| 5,724,984 A | 3/1998 | Arnold et al. |
| 5,795,303 A | 8/1998 | Swanson et al. |
| 6,148,233 A | 11/2000 | Owen et al. |
| 6,280,463 B1 | 8/2001 | Dupelle et al. |
| 6,453,205 B1 | 9/2002 | Dupelle et al. |
| 6,505,067 B1 | 1/2003 | Lee et al. |
| 6,546,285 B1 | 4/2003 | Owen et al. |
| 6,847,836 B1 | 1/2005 | Sujdak |

(Continued)

FOREIGN PATENT DOCUMENTS

JP  2001-170190  6/2001

*Primary Examiner* — Eric D. Bertram
(74) *Attorney, Agent, or Firm* — Fish & Richardson P.C.

(57) ABSTRACT

Electrodes and circuitry for monitoring and stimulating the exterior of the human body, comprising delivering stimulation pulses to stimulation electrodes applied to the exterior of the body, detecting an electrical potential at monitoring electrodes applied to the exterior of the body, positioning at least a first and second monitoring electrode at locations at which an electrical artifact caused by the electrical stimulation pulses is substantially cancelled in a signal formed from the electrical potentials detected at the first and second monitoring electrodes.

34 Claims, 15 Drawing Sheets

(56) References Cited

U.S. PATENT DOCUMENTS

2003/0171685 A1* 9/2003 Lesser et al. ............ 600/509
2004/0176674 A1 9/2004 Nazeri
2004/0267145 A1 12/2004 David
2006/0178041 A1 8/2006 Lund et al.

* cited by examiner

MONITORING PHYSIOLOGICAL SIGNALS DURING EXTERNAL ELECTRICAL STIMULATION

CROSS-REFERENCE TO RELATED APPLICATIONS

This application is a divisional application of and claims priority to U.S. application Ser. No. 11/055,572, filed on Feb. 10, 2005, now U.S. Pat. No. 8,185,199. This application is hereby incorporated by reference.

TECHNICAL FIELD

This invention relates to monitoring physiological signals (e.g., ECG signals) on the exterior of a patient during external electrical stimulation (e.g., pacing) of the patient.

BACKGROUND

It is often desirable to monitor physiological signals during or after delivery of electrical stimulation to a patient. For example, ECG signals are typically monitored during external cardiac pacing. But the electrical stimulation can produce stimulus artifacts in the monitored signal. To reduce the magnitude of such artifacts, monitoring electrodes are often intentionally placed at a considerable distance from stimulation electrodes. The stimulus artifact is attenuated by distance through the body and has less effect on the measured physiological signals of interest. For example, standard ECG lead placement for monitoring a patient during external cardiac pacing is shown in FIG. 1. Two ECG leads are placed high on the chest near each arm, and a third low on the chest near one leg, all at a considerable distance from the stimulation electrodes. To achieve this distant placement of the monitoring electrodes, the caregiver must typically place five separate electrodes on the patient, and connect separate monitoring cables to each of the ECG electrodes (typically, the stimulation electrodes have cables pre-connected).

An alternative to separate, remotely positioned monitoring electrodes is using the stimulation electrodes for both stimulation and monitoring. Monitoring could, in theory, be done during intervals between stimulation pulses, but a large stimulus artifact is typically present for much of that interval, and thus it has not typically been practical to use the stimulation electrodes for ECG monitoring during pacing. For example, the ECG signal induced by the pacing pulse often occurs within 200 milliseconds subsequent to the pacing pulse and before the artifact has sufficiently attenuated to allow for adequate monitoring.

The stimulus artifact during pacing can make the ECG difficult to interpret, even when the ECG is detected on remotely positioned monitoring electrodes. It is generally required that the ECG be clean enough so that the effectiveness of pacing can be assessed and the stimulus energy adjusted as needed. The stimulus artifact is often so large as to make that assessment difficult or impossible.

Internal pacing involves much lower currents applied directly to the heart and monitoring through the stimulation electrodes has been accomplished in the prior art. The problem of stimulus artifacts in the ECG signal principally arises with external pacing where the higher currents and larger therapy electrodes require the use of separate monitoring electrodes located at a sufficient distance. A similar problem exists during external cardiac defibrillation, but there is less need to detect an ECG signal within milliseconds after the stimulus as is the case with pacing.

Electrical stimulation requires the delivery of an electrical current to the body. Current flows from one stimulation electrode to the other, and often results in the stimulation electrodes becoming polarized following delivery of a stimulation pulse (opposite polarity charge buildup on the two electrodes). A stimulus artifact is seen on the monitoring electrodes both during and after the stimulation pulse, with the amplitude of the artifact typically depending on the position of the monitoring electrode in the electric field created by the difference in potential on the two stimulation electrodes.

Physiological monitoring systems typically amplify the potential difference(s) between monitoring electrodes. The signals of interest are often much smaller in magnitude than the stimulus artifact. Thus, the artifact often masks the physiological signals or saturates the circuitry used for monitoring. Certain applications require acquisition of physiological waveforms during or immediately after the stimulus (e.g., cardiac pacing), and the presence of the stimulus artifact is problematic.

Some efforts have been undertaken to mitigate the effect of the stimulus artifact on the physiological monitoring. Way U.S. Pat. Nos. 4,955,381 and 5,080,099 proposed an electrode assembly in which a separate monitoring electrode was spaced a short distance from the stimulus electrode in a single assembly. Dupelle et al. U.S. application Ser. No. 10/958,987, filed on Oct. 5, 2004 teaches providing a depolarizing current following a stimulus to reduce the polarization artifact. Hauck et al. U.S. Pat. No. 5,330,512 taught a solution for implanted electrodes wherein the stimulus is much lower than for external electrodes, and the implanted leads have a much smaller surface area than pads of external electrodes.

SUMMARY

We have discovered that in external pacing the effect of the stimulus artifact on physiological monitoring can be reduced if a plurality of external monitoring electrodes across which a potential is measured are configured so that the artifact is substantially cancelled out in a signal formed from the electrical potentials detected at the two monitoring electrodes.

In a first aspect, the invention features a device-implemented method of monitoring and stimulating the exterior of the human body with electrodes, comprising delivering stimulation pulses to stimulation electrodes applied to the exterior of the body, detecting an electrical potential at monitoring electrodes applied to the exterior of the body, positioning at least a first and second monitoring electrode at locations at which an electrical artifact caused by the electrical stimulation pulses is substantially cancelled in a signal formed from the electrical potentials detected at the first and second monitoring electrodes.

Preferred implementations of this aspect of the invention may incorporate one or more of the following. The signal formed from the electrical potentials may comprise a difference signal that comprises a difference between the electrical potentials detected at the first and second monitoring electrodes. The first and second monitoring electrodes may be at locations at which the electrical artifact is substantially equal. The stimulation pulses may comprise cardiac stimulation pulses, and the difference signal may comprise an ECG signal. The cardiac stimulation pulses may comprise pacing pulses. There may be at least three monitoring electrodes applied to the exterior of the patient, and the first and second monitoring electrodes may be selected from among the at least three monitoring electrodes, with the selection being made so as to reduce the effect of the electrical artifact on the difference signal. The selection of first and second monitoring electrodes may be made automatically by the device rather than manually by the user. The automatic selection of the first and second monitoring electrodes may vary over time. The at least three monitoring electrodes may comprise at least two monitoring electrodes positioned at different distances from one of the stimulation electrodes, and wherein the selection of the first monitoring electrode may comprise choosing between the two electrodes positioned at different distances. The choosing between the two electrodes may vary over time. The invention may further comprise at least a third monitoring electrode applied to the exterior of the patient, and wherein the difference signal may comprise the difference between the electrical potential detected at the first electrode and a combination of the electrical potential detected at the second and third electrodes. The manner in which the combination is made may vary over time to compensate for variation over time of the relative magnitude of the electrical artifact at the second and third electrodes. The invention may also further comprise at least a fourth monitoring electrode applied to the exterior of the patient, and wherein the difference signal may comprise the difference between a combination of the electrical potential detected at the first and fourth electrodes and a combination of the electrical potential detected at the second and third electrodes. One or both of the combination of the electrical potential detected at the first and fourth electrodes and a combination of the electrical potential detected at the second and third electrodes may vary over time. The edge-to-edge separation between the active areas of the at least first and second monitoring electrodes and the active area of one of the stimulation electrodes may be less than 10 centimeters. The at least first and second monitoring electrodes may be positioned at the same separation from one of the stimulation electrodes. The invention may further comprise a third monitoring electrode positioned at the same separation as the first and second electrodes from one of the separation electrodes. The first and second monitoring electrodes and the one stimulation electrode may be fixed in position on a common substrate. The at least first and second monitoring electrodes may be positioned so that they are at approximately the same electrical potential in an electric field formed between the two stimulation electrodes when the stimulation electrodes are polarized following a stimulation pulse. The at least first and second monitoring electrodes may be positioned along approximately the same field line in an electric field formed between the two stimulation electrodes when the stimulation electrodes are polarized following a stimulation pulse. The first and second monitoring electrodes may be supported on a first substrate that is separate from a second substrate supporting one of the stimulation electrodes. The first substrate supporting the first and second monitoring electrodes may substantially surround the second substrate. The first substrate may be annular in shape and the second substrate may be circular in shape, and the two substrates may be positioned approximately concentrically, so that the separation between the two may be approximately an equal radial distance. The at least first and second monitoring electrodes and the at least one stimulation electrode may form one assembly. The positions of the at least first and second monitoring electrodes and the stimulation electrode may be fixed on the assembly, so that the separation between each of the monitoring electrodes and the stimulation electrode may be fixed. Electrical artifact potential in the ECG difference signal may be less than about 10 millivolts measured within 100 milliseconds after termination of the cardiac pacing pulse. The electrical artifact potential in the ECG difference signal may be less than five times the QRS amplitude when the pacing pulses are of sufficient amplitude to capture the heart.

Detecting an electrical potential at monitoring electrodes may comprise an impedance matching circuit to which at least the first and second monitoring electrodes may be connected. The impedance matching circuit may create an imbalance in the electrode impedances to compensate for variation in the electrical artifact potential in the two monitoring electrodes. There may be a plurality of difference signals, and the difference signals may be used in a transformation to derive ECG signals that resemble standard 3-lead ECG signals.

The invention may also further comprise having a monitoring device automatically identify a nonstandard monitoring configuration from one or more of the electrodes or from a connector used to the connect the electrodes to the monitoring device, and in the event of identifying the nonstandard monitoring configuration automatically modifying signal processing of the detected electrical potentials. The invention may further comprise positioning a third electrode on the body, and wherein the signal formed from the electrical potentials may comprise a summation of electrical potentials measured at the first and second electrodes with respect to the third electrode, and wherein the electrical artifact may be substantially cancelled in the signal as a result of the electrical artifact being of similar magnitude but of opposite polarity in the electrical potentials measured. There may be at least first and second stimulation electrodes, and the first monitoring electrode may be positioned in the vicinity of the first stimulation electrode, and the second monitoring electrode may be positioned in the vicinity of the second stimulation electrode. The signal may be formed in a manner that is varied over time. The signal may be formed by forming a combination of the electrical potentials at the first end and second monitoring electrodes, and the manner in which the combination is made may be varied over time.

In a second aspect, the invention features a method of external monitoring and external stimulating the heart, comprising delivering stimulation pulses between a first polarity stimulation electrode and a second polarity stimulation electrode applied to the exterior of the body, wherein at least the first polarity stimulation electrode comprises a plurality of smaller electrodes, through which the stimulation pulses are applied, wherein the aggregate area of the smaller electrodes is sufficient for stimulation; and monitoring an ECG potential by forming a difference signal that comprises the difference between the electrical potentials detected at two of the smaller electrodes, wherein the two smaller electrodes used to form the difference signal are positioned and configured so that the stimulus artifact from polarization is approximately equal on both of the smaller electrodes, so that the stimulus artifact is approximately cancelled in the difference signal.

Preferred implementations of this aspect of the invention may incorporate one or more of the following. The stimulation pulses may comprise cardiac pacing pulses applied to the exterior of the chest.

In a third aspect, the invention features an electrode assembly for external cardiac pacing and external cardiac monitoring, comprising at least one external stimulation electrode for delivering a pacing pulse, at least first and second external monitoring electrodes, at least one positioning element to which the stimulation and first and second monitoring electrodes are connected, wherein the positioning element, stimulation electrode, and first and second monitoring electrodes are configured so that the first and second monitoring electrodes are located in positions in which an electrical artifact caused by the pacing pulses is substantially cancelled in a difference signal formed by taking a difference between the electrical potentials detected at the first and second monitoring electrodes.

Preferred implementations of this aspect of the invention may incorporate one or more of the following. The positioning element may comprise a common substrate that supports the stimulation electrode and the first and second monitoring. The positioning element may comprise elements such as wires that prescribe the separation of the first and second monitoring electrodes from the stimulation electrode. The edge-to-edge separation between the active areas of the at least first and second monitoring electrodes and the active area of one of the stimulation electrodes may be less than 10 centimeters. The at least first and second monitoring electrodes may be positioned at the same separation from one of the stimulation electrodes. The invention further comprises a third monitoring electrode positioned at the same separation as the first and second electrodes from one of the separation electrodes. The at least first and second monitoring electrodes may be positioned so that they are at approximately the same electrical potential in an electric field formed between the two stimulation electrodes when the stimulation electrodes are polarized following a stimulation pulse. The at least first and second monitoring electrodes may be positioned along approximately the same field line in an electric field formed between the two stimulation electrodes when the stimulation electrodes are polarized following a stimulation pulse. The first and second monitoring electrodes may be supported on a first substrate that is separate from a second substrate supporting one of the stimulation electrodes, and the first and second substrates may be shaped to facilitate their being applied to the patient in a desired relative position. The first substrate may be annular in shape and the second substrate may be circular in shape, and the two substrates may be positioned approximately concentrically, so that the separation between the two may be approximately an equal radial distance. The first and second monitoring electrodes and the stimulation electrode may form one assembly. The positions of the at least first and second monitoring electrodes and the stimulation electrode may be fixed on the assembly, so that the separation between each of the monitoring electrodes and the stimulation electrode may be fixed.

In a fourth aspect, the invention features an electrode assembly for external cardiac pacing and external cardiac monitoring, comprising at least one external stimulation electrode for delivering a pacing pulse, the stimulation electrode comprising a stimulation conductive plate, at least one external monitoring electrode, the monitoring electrode comprising a monitoring conductive plate, a backing layer supporting the stimulation and monitoring electrodes, wherein the stimulation conductive plate and monitoring conductive plate are spaced apart, a common gel layer in electrical contact with both the stimulation electrode and the monitoring electrode.

Preferred implementations of this aspect of the invention may incorporate one or more of the following. The common gel layer may comprise solid gel or hydrogel.

In a fifth aspect, the invention features an electrode assembly for external cardiac pacing and external cardiac monitoring, comprising at least one external stimulation electrode for delivering a pacing pulse, the stimulation electrode comprising a stimulation conductive plate, at least one external monitoring electrode, the monitoring electrode comprising a monitoring conductive plate, a backing layer supporting the stimulation and monitoring electrodes, wherein the stimulation conductive plate and monitoring conductive plate are spaced apart, a first gel layer in electrical contact with the stimulation electrode, a second gel layer in electrical contact with the monitoring electrode, wherein the first and second gel layers are spaced apart, wherein one of the first gel layer or the second gel layer comprises a solid gel or hydrogel, and wherein the other one of the first gel layer or the second gel layer comprises a liquid gel.

In a sixth aspect, the invention features an electrode assembly for external stimulation and/or monitoring of a patient, the assembly comprising at least a first and second electrode supported within the assembly, a first gel layer positioned adjacent the first electrode, a second gel layer positioned adjacent the second electrode, the first and second gel layers having different levels of moisture content, and a moisture vapor barrier layer sized and positioned to retard moisture vapor from migrating from one of the first and second gel layers to the other of the gel layers.

Preferred implementations of this aspect of the invention may incorporate one or more of the following. The electrode assembly may be configured for cardiac stimulation, and the first electrode may comprise a stimulation electrode and the second electrode may comprise a monitoring electrode. The first gel layer may comprise a liquid gel and the second gel layer may comprise a solid gel. The first gel layer may comprise a solid gel of one moisture content, and the second gel layer may comprise a solid gel of a second moisture content greater than the first content. The vapor barrier may comprise a polyester film. The vapor barrier may comprise an aluminum film.

In a seventh aspect, the invention features a multi-electrode assembly for cardiac stimulation and monitoring, the assembly comprising a monitoring electrode configured to monitor electrical potential on the chest of a patient, a stimulation electrode configured to deliver one or more stimulating pulses to the chest of a patient, an electrode cable having first and second cable ends, the first cable end configured for connection to an external cardiac device and the second cable end configured for connection to the monitoring electrode and to the stimulation electrode, and a non-linear circuit element electrically interposed between the second cable end and the stimulation electrode, the non-linear circuit element being configured to conduct during delivery of the stimulating pulses and to block conduction in the presence of a residual potential on the stimulating electrode following delivery of a stimulation pulse.

Preferred implementations of this aspect of the invention may incorporate one or more of the following. The non-linear circuit element may comprise one or more diodes or gas discharge tubes. The non-linear circuit element may comprise at least two non-linear circuit elements forming parallel paths between the cable and the stimulation electrode, and with the polarity of the elements being opposite along the two paths, so that a biphasic stimulation waveform can be delivered to the stimulation electrode, with current flowing through one of the paths in one polarity of the waveform and through the other of the paths in the other polarity of the waveform. Conductance in the presence of a residual potential on the stimulation electrode may be blocked along one of the parallel paths by setting the net offset potential of the one or more elements in that path to greater than the expected residual potential. The non-linear circuit element may comprise one or more transistors. The non-linear circuit element may generally block current flow in one direction and may permit current flow in the opposite direction. The electrode cable may comprise a single conductor, and the first and second cable ends may be first and second ends of the single conductor. The invention may further comprise a high-impedance element that is positioned in the electrical path between the electrode cable and the monitoring electrode and configured to reduce the level of current flowing to the monitoring electrode during delivery of a stimulation pulse to the stimulating electrode.

Among the many advantages of the invention (some of which may be achieved only in some of its various aspects and implementations) are the following: Reducing the stimulation artifact has the advantage that stimulation and monitoring electrodes may be placed in close proximity on the exterior of the body. This allows, for example, one stimulation and one or more monitoring electrodes to be combined optionally in a single assembly. With multiple electrodes combined in one assembly, cabling and connections between the electrodes and the stimulation/monitoring device can also be improved. Combining the monitoring and stimulation electrodes in one assembly can be a great help in emergency situations, as it can reduce the time required to apply and connect the electrodes.

Other features and advantages of the invention will be found in the detailed description, drawings, and claims.

DETAILED DESCRIPTION

Figure 1:
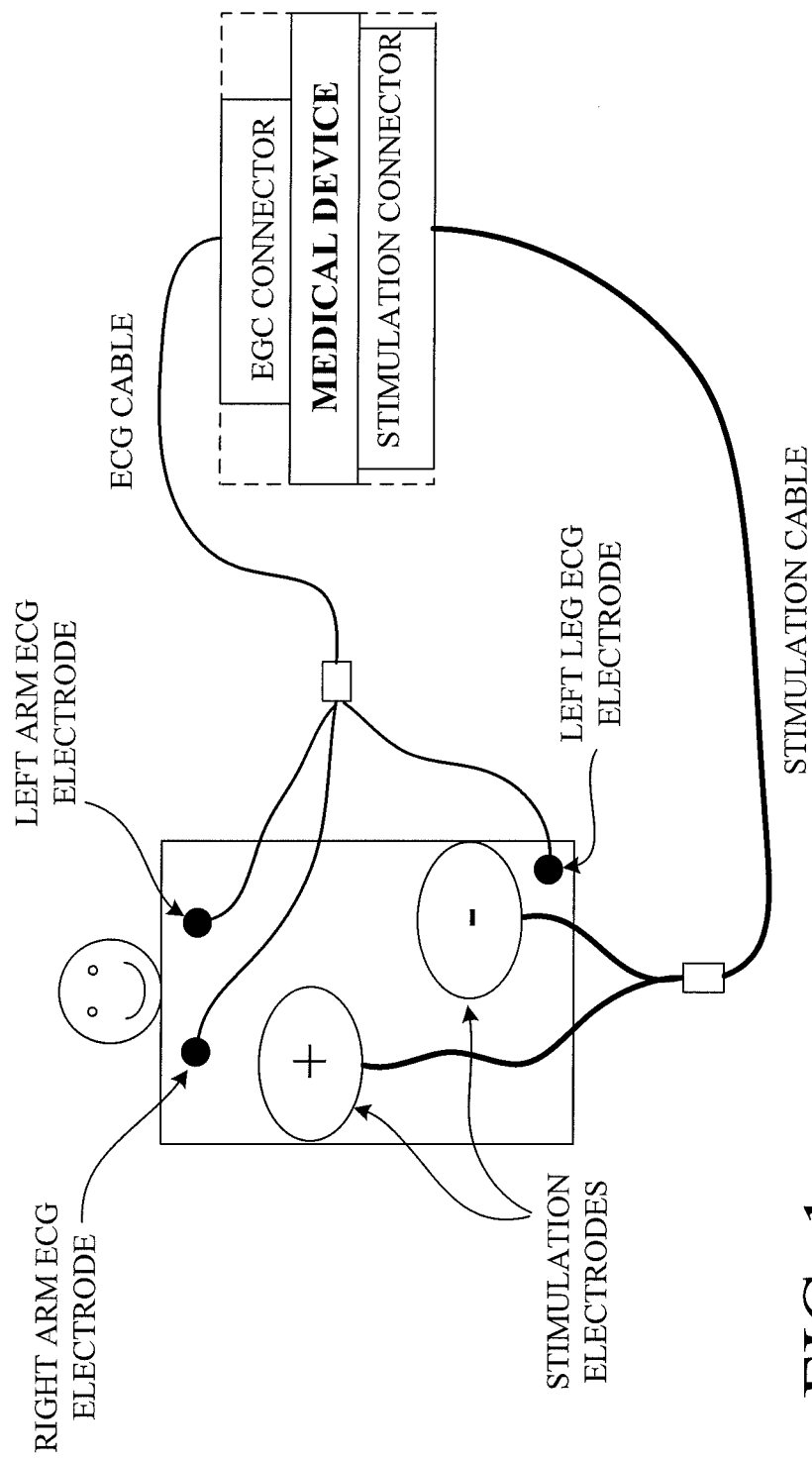
FIG. 1 is a schematic of a prior art arrangement of stimulation and monitoring electrodes.
Figure 2:
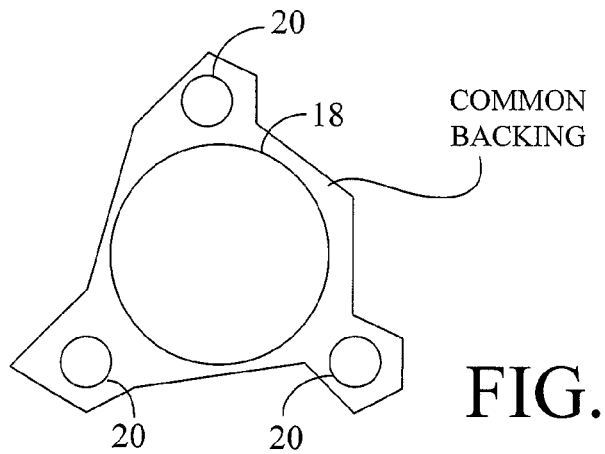
FIG. 2 is a diagrammatic, plan view of one implementation of a plurality of monitoring electrodes positioned near a stimulation electrode.

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

One implementation is illustrated in FIGS. 2 and 15-17. A front electrode 14 includes three monitoring electrodes 20 positioned equidistant from a central stimulation electrode 18. All three monitoring electrodes 20 and the stimulation electrode 18 are supported on a common assembly. A back electrode 12 includes only a stimulation electrode 16, but may optionally also include one or more integrated monitoring electrodes as well.

Figure 16:
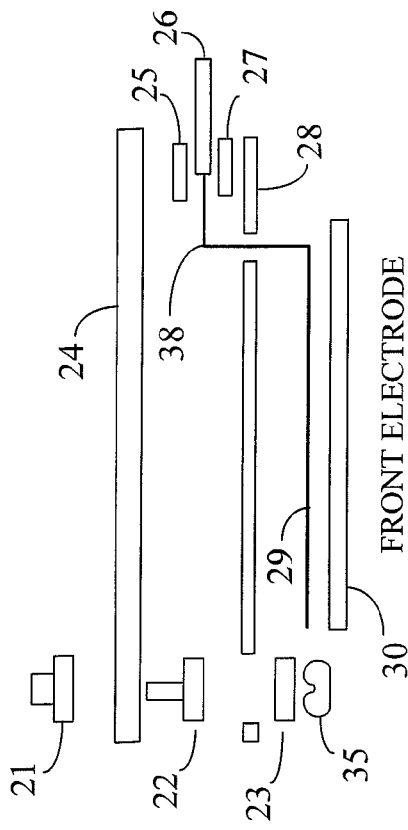
FIG. 16 is a cross-sectional, exploded view taken along 16-16 of FIG. 15, showing the construction of the front electrode.
Figure 17:
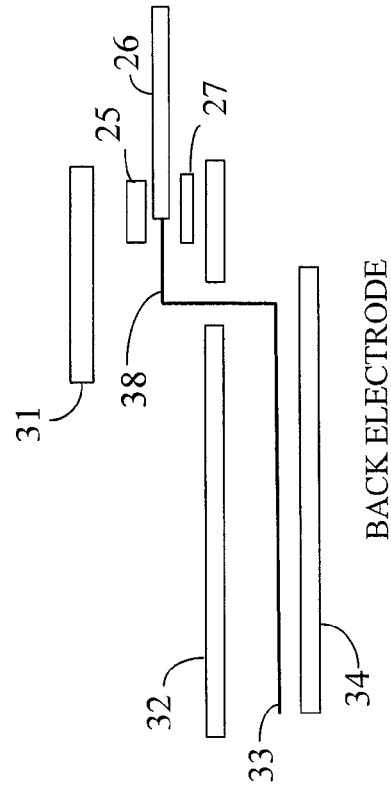
FIG. 17 is a cross-sectional, exploded view taken along 17-17 of FIG. 15, showing the construction of the posterior (or back) electrode.
Figure 15:
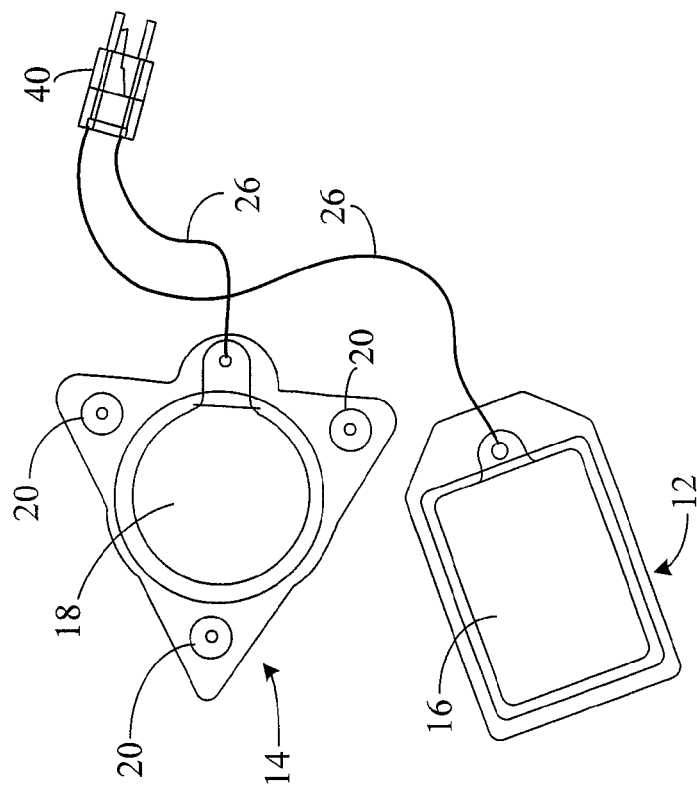
FIG. 15 is a plan view of an implementation in which two chest electrode assemblies, the front assembly having a stimulation electrode and three monitoring electrodes, and the back assembly having just a stimulation electrode, have a common electrical connector for stimulation.

The active area of the stimulation electrode is about 10 cm in diameter. The active area of each monitoring electrode is about 2 cm in diameter. The edge of each monitoring electrode active area is spaced about 1 cm from the edge of the adjacent stimulation electrode active area Various constructions are possible for the electrode pad assemblies. FIGS. 16-17 show one possible construction. Materials have been chosen that provide resiliency and compliance to the skin surface. FIG. 16 shows the electrode assembly configured to be applied to the front of the chest. A foam cover (or backing) layer 24 (e.g., Voltek Volara™) extends fully across the back of the electrode (top surface facing up away from patient). Each of the three monitoring electrodes is formed by securing a nickel plated brass snap 21 to an AgCl post 22 through an opening in the cover layer (alternatively a lead wire may be connected to the monitoring electrodes). Below that is a foam frame layer 28, which has an opening through which each of the AgCl posts (AgCl plated glass filled ABS) contact a porous foam sponge 23, which is impregnated with ECG gel 35 (e.g., Pharmaceutical Innovations™ QR). The stimulation electrode 18 is provided by a conductive plate 29 (e.g., tin) in the center of the electrode assembly. The conductive plate is supported beneath the foam frame layer 28. Beneath the conductive plate, and making conductive contact with the patient, is a conductive layer 30, e.g., a solid gel such as a hydrogel (e.g., Ludlow™ 63T hydrogel). At one edge, a portion 38 of the conductive plate extends through an opening in the foam frame layer, and is mechanically and electrically connected at 25 to a wire lead 26. Wire lead 26 extends to an electrical connector 40, to which the wire lead 26 from the back electrode assembly is also connected.

Various alternatives may be used for the conductive, skin-contacting layers 23, 30. These include, but are not limited to, solid conductive gels (e.g., hydrogel), a porous material filled with a liquid gel, and a porous material soaked in a conductive solution such as saline.

FIG. 17 shows the electrode assembly configured to be applied to the back of the chest. It has a similar construction to that of the front electrode, except that it lacks monitoring electrodes, and has a rectangular, rather than circular, stimulation electrode. Conductive plate 33 is supported on the underside of a foam backing layer 32. A conductive layer 34, e.g., solid gel such as the same hydrogel as used in the front stimulation electrode, makes contact with the patient. A portion 38 of the conductive plate extends through an opening in backing layer 32, and is connected to wire lead 26. An insulator foam backing layer 31 covers the portion 38 of the conductive plate that extends to the top of foam backing layer 32.

In the implementation of FIGS. 2 and 15-17, the monitoring electrodes 20 are all positioned the same distance from the stimulation electrode 18. If the electrical currents flowing between the stimulation electrodes are approximately equal in all directions then the artifact measured by each monitoring electrode will be similar and cancel when a potential difference is formed by subtracting the signals. But placing the monitoring electrodes at equal distances from the stimulation electrode is no guarantee that the measured stimulus artifact will be the same in all three monitoring electrodes. Transmission factors, monitoring electrode impedance, the path of current flow, the shape of the electric field, and other variables can influence measured artifact. Some of the transmission factors, e.g., respiration and blood flow, may be time varying. Current flow can be influenced by surface properties and anatomical structures in the body.

However, positioning the monitoring electrodes equal distances from the stimulation electrode may be sufficient in many cases, as it may result in stimulus artifacts that are sufficiently closely matched as to reduce the level of artifact to an acceptable level in the differential signal (the difference in potential between two monitoring electrodes). And the remaining artifact can optionally be reduced further using other methods described below.

Alternatively, the monitoring electrode spacing can be adjusted based on modeling current flows, experimental results, or a priori knowledge of the transmission factors involved. Circuitry in the electrode or in the medical device doing the monitoring may equalize the artifact measured at each electrode by changing a gain or impedance, or by using other known techniques.

Forming the sum of two monitoring electrodes with artifacts of similar magnitude but opposite polarity will also reduce artifact, e.g., the sum of monitoring electrodes relative to a common reference where one is positioned near the positive and one near the negative stimulation electrodes.

In the implementation of FIGS. 2 and 15-17, three monitoring electrodes are provided for the front electrode assembly, which is positioned over the heart. The back electrode assembly does not have any monitoring electrodes. Other implementations may use different numbers of monitoring electrodes on the front assembly, and monitoring electrodes could be included on the back assembly. Measuring a potential difference requires at least two electrodes. Integration of three monitoring electrode with the stimulation electrode over the heart has at least two benefits. First, many ECG monitors use a third electrode to drive common mode signals back to the patient, to improve signal quality in the presence of large common mode signals such as power line interference. If the third electrode is only used for this common mode rejection purpose, its location relative to the stimulation electrode is less important. Second, ECG monitors for three-lead monitoring generally display the potential difference between a selected electrode pair. These differences are called Lead I, Lead II, and Lead III when the electrodes are positioned in conventional locations on the right and left arms as well as the left leg. The monitoring electrodes in the invention do not represent the standard Leads, but still provide three possible potential differences, from which the operator of the ECG monitor may select. The operator may select the view which is most clinically relevant or contains the least artifact during cardiac pacing. In implementations in which three potential differences between pairs of electrodes are sought, the locations of all three monitoring electrodes can be selected to improve artifact cancellation (e.g., each may be equidistant from the central stimulation electrode), so that a choice can be made as to the best two electrodes to use for canceling the stimulus artifact. More than three monitoring electrodes may also be provided.

The monitoring hardware may be configured to detect the artifact-reducing electrode assembly. If it recognizes such an electrode assembly, the hardware may process signals differently and/or change labeling on displays, strip chart recorders, storage devices and external interfaces. The change in labeling will prevent those reviewing the signals from trying to interpret them as a standard electrode configuration (e.g., standard 3-lead). The electrode assembly identification would typically be made through the monitoring portion of the assembly rather than through the stimulation portion, because in some implementations electrical stimulation is allowed to continue even if a switch is made to standard monitoring electrodes when time permits.

Various methods may be used to identify the electrode assembly, including, for example, the following: (1) specific resistances between connector pins are detected by the monitor; (2) voltages, currents, or specific waveforms input to the monitor from the electrode assembly; (3) interfaces to non-volatile memory or a microprocessor contained within the electrode connector or assembly; (4) pulling unused monitoring channels to specific voltages (currents, or known waveforms) that can be used to identify the cable. An example of the fourth option is connecting a three lead ECG cable to a 10 wire monitor with a special electrode connector so that certain unused inputs are shorted to ground while others are shorted to a specified voltage. Any condition that is unlikely to occur without the connector in place can be used for identification.

Figure 11:
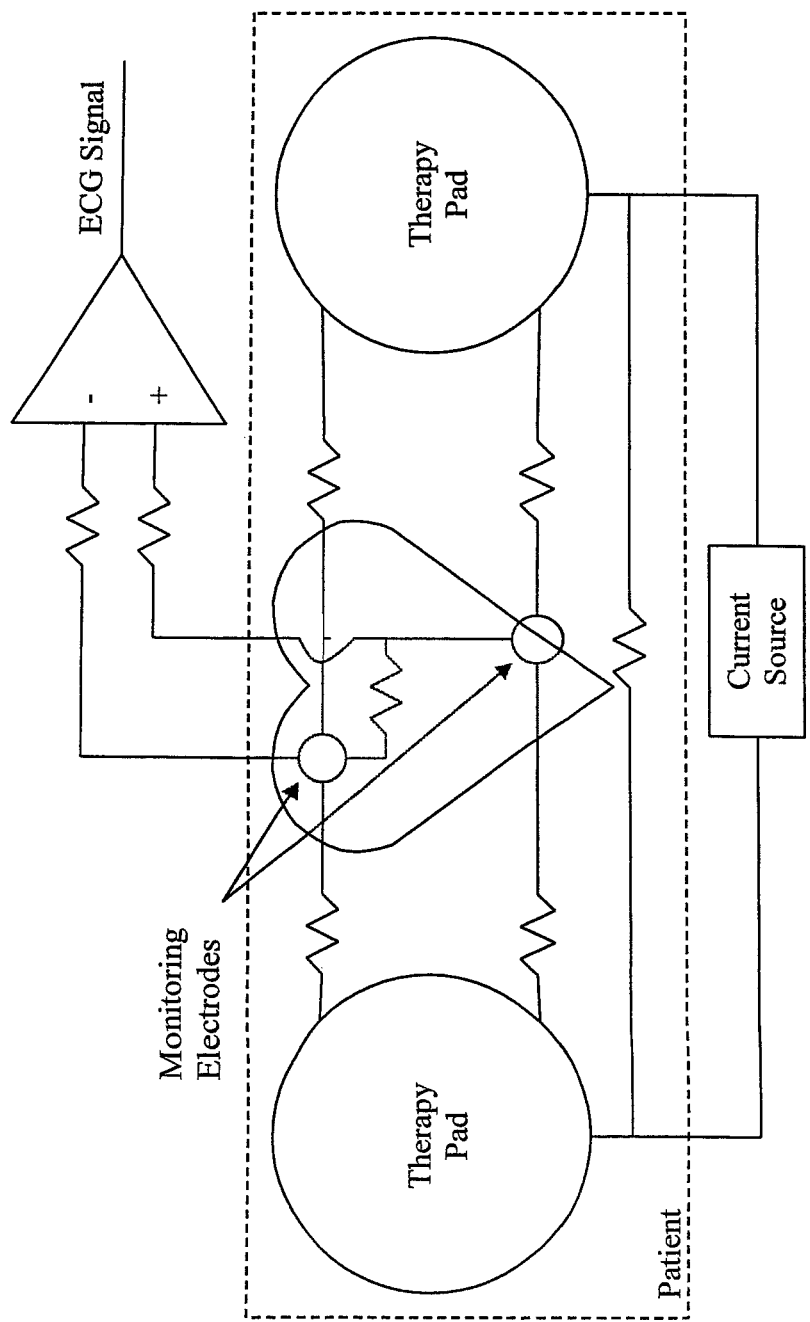
FIG. 11 is a schematic illustrating the physics of current flow between two stimulation electrodes and ECG signal detection from two monitoring electrodes.

FIG. 11 illustrates the physics underlying the ability of some implementations to cancel much of the stimulus artifact from the ECG signal. A stimulus is applied to the patient (represented by the dashed line rectangle) using a pair of stimulus electrodes (therapy pads). Current flows from one therapy pad to another along varying current paths. The figure shows the overly simplified case of there being just three current paths, with one monitoring electrode positioned along each of two of the paths. Resistors are shown along the current paths to represent the resistance experienced by current flowing along particular paths. The values of the resistors are dependent on the placement of the electrodes, and the physical properties of the patient, and the values of the resistors may be time varying (e.g., as the result of respiration).

Each monitoring electrode records some potential owing to the current flowing during a therapy pulse. After the pulse, the therapy pads may remain polarized. The polarization equalizes over time, and the monitoring electrodes record the potential difference due to the polarization. If the polarization has an equal effect on both monitoring electrodes, then the effect of the polarization (what we have called the stimulus artifact) will cancel, and the differential signal will be due to the electrical activity within the body such as the ECG.

Figure 3:
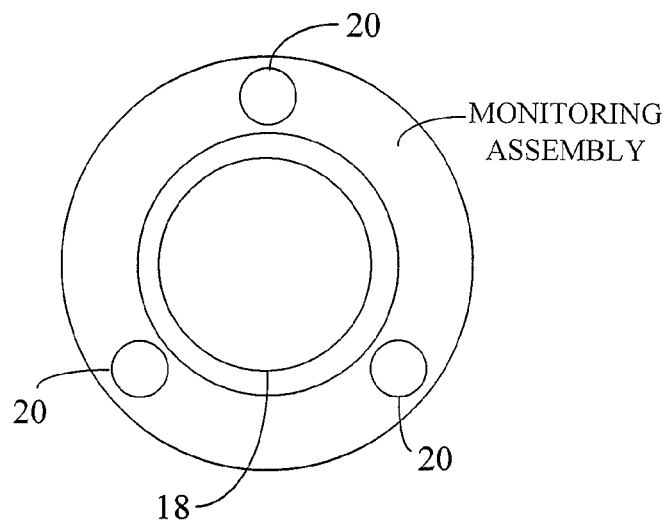
FIG. 3 is a diagrammatic, plan view of another implementation of a plurality of monitoring electrodes positioned near a stimulation electrode.

Another possible implementation is shown in FIG. 3. The monitoring electrodes 20 are supported on a common assembly separate from (but, in this example, surrounding) the stimulation electrode 18. In FIG. 3 the common assembly is an annular in shape to surround a circular stimulation electrode, but other shapes may be used. An advantage of the shapes used in FIG. 3 is that they help guarantee that the monitoring electrodes are equally spaced from the stimulation electrode. Two of the monitoring electrodes are positioned to be equidistant from the stimulation electrode. The third monitoring electrode (at the top of the figure) is shown in a position slightly away from an equidistant location. If the third electrode is not used to form an ECG signal, but is used only for common mode rejection purposes, then it is not necessary that it be equidistant. In other implementations, in which it was sometimes desirable to use the third electrode for forming an ECG signal, it may be decided to place it in an equidistant location just as the other two monitoring electrodes.

Figure 4:
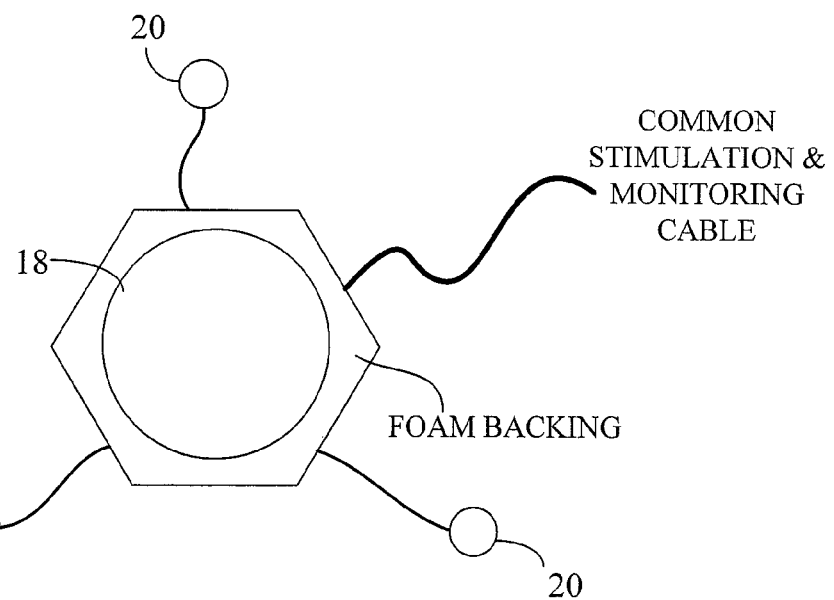
FIG. 4 is a diagrammatic, plan view of another implementation of a plurality of monitoring electrodes positioned near a stimulation electrode.

Other methods may also be suitable for positioning the electrodes. They may be positioned at set distances from the therapy pad using constant length cables or other physical connection to the therapy pad that allows easy placement at a pre-determined distance. FIG. 4 illustrates one implementation in which placement of the monitoring electrodes around the stimulation electrode is regulated by the length of electrode lead wires extending from the central stimulation electrode. When the wires are fully extended in a radial direction, the electrode positions will be equidistant from the stimulation electrode. Similarly, the wires may be slightly different lengths in order to equalize artifact based on a priori knowledge of the current flow. Alternatively, the separation between monitoring and stimulation electrodes could be prescribed by a mechanical element (e.g., a mechanical cable), rather than by the electrical leads. The electrodes might initially be affixed (prior to their extension) to the therapy pad by an adhesive or a mechanical device (i.e. clip, Velcro, etc).

Figure 6:
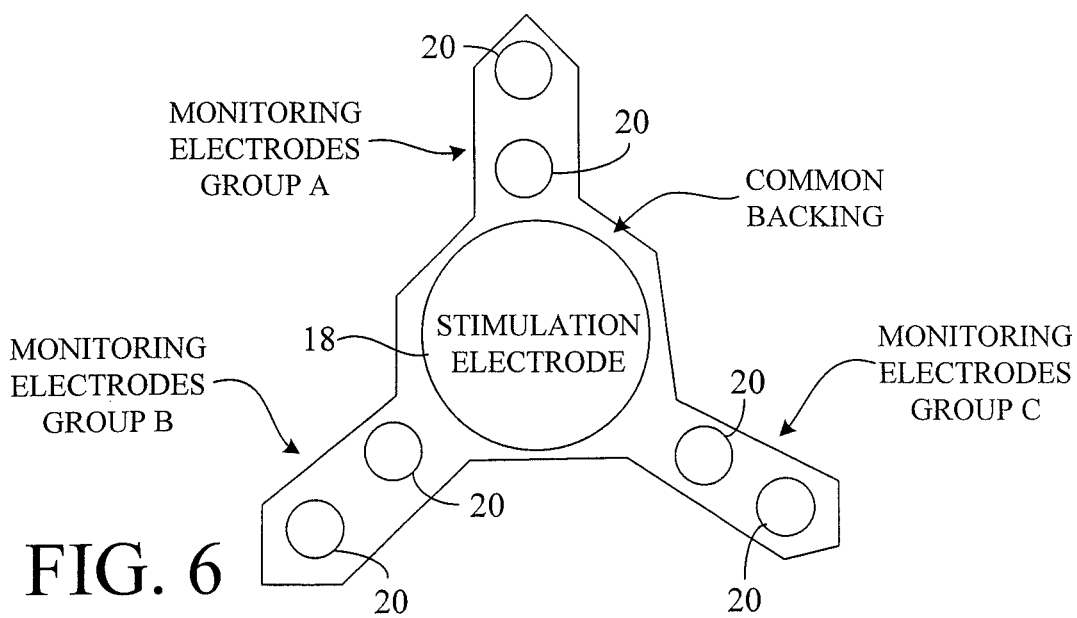
FIG. 6 is a diagrammatic, plan view of another implementation of a plurality of monitoring electrodes positioned near a stimulation electrode.

Another implementation is shown in FIG. 6. Three groups of multiple monitoring electrodes—with the electrodes in each group being at different locations relative to the stimulation electrode—are shown. In FIG. 6, there are two monitoring electrodes 20 in each of Group A, B and C. Analog or digital signal processing may be used to produce a combination of the electrodes in a group, so that when the difference between the processed (or weighted) combinations from two groups is taken the artifact is better cancelled in the differential signal. This method provides compensation for irregularities in the current flow or electric field originating from the stimulation electrode, and may be time-varying to compensate for time-varying parameters such as respiration. More than two electrodes may be provided in each group. Not all locations will require forming a weighted combination of a plurality of electrodes.

Synthesized Leads

Figure 7:
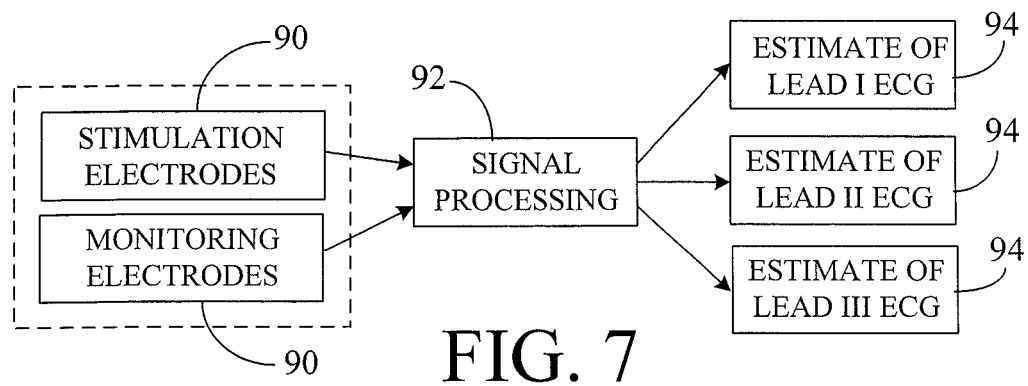
FIG. 7 is a block diagram of one implementation of deriving an estimate of standard 3-lead ECG signals by transforming the non-standard ECG signals detected using the electrodes shown herein.

Good electrode placements for artifact rejection may not be ideal for analysis of monitored signals. E.g., they may not provide a standard clinical ECG signal. Signal processing may be used to derive or synthesize improved or more clinically standardized looking waveforms from the actual monitoring electrodes. This may be accomplished by, in effect, creating a derived (or synthesized) monitoring electrode from combinations of actual monitoring electrodes. A block diagram of one cardiac pacing implementation of this procedure is shown in FIG. 7. Signals 90 from monitoring electrodes (e.g., ones of the type shown in FIG. 2) may optionally be combined with signals from one (or both) stimulation electrode (which during intervals between stimulation pulses can also serve as a monitoring electrode). A signal processing block 92 produces estimates 94 of standard ECG vectors that are more familiar to the user than potential differences formed directly from the nonstandard electrode locations of FIG. 2.

A preferred implementation is to transform the signals from the monitoring electrodes (and optionally the stimulation electrode) into ECG signals comparable to what would have been detected using the standard 3-lead placement of ECG electrodes (two near the arms, and one near a leg).

To perform the transformation, the coefficients of a linear transformation matrix are derived from a statistically meaningful population of patients, from whom ECG measurements have been taken at both the new monitoring electrode (and stimulation electrode) locations and the conventional 3-lead locations. A least squares fit is done to derive coefficients of the linear transformation matrix.

The prior art taught several methods of synthesizing leads from a reduced or alternate set of electrodes. For instance, Dower's EASI system (U.S. Pat. No. 5,711,304) used five electrodes in non-standard locations on the body to synthesize an estimate of the 12-Lead ECG. Dower placed the electrodes far apart on the body in locations selected for ease of placement and 12-Lead synthesis. The prior art also taught transformations from implanted leads to standardized leads Implanted electrodes are fixed in position. It is possible to attach standard surface electrodes to the patient and derive the optimal transform.

Figure 18:
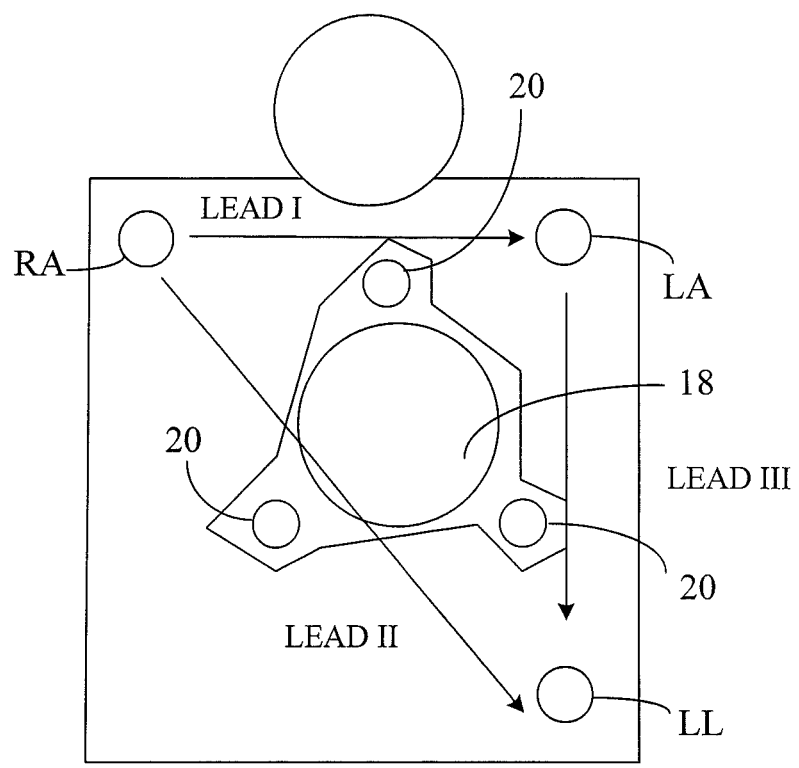
FIG. 18 is a diagrammatic plan view of the implementation of FIG. 2 and the locations of standardized, 3-lead electrodes.

FIG. 18 and the following discussion provide one mathematical basis for the lead synthesis. The figure shows a round stimulation (pacing/defibrillation) electrode surrounded by three equidistant monitoring electrodes, each spaced from the others at 120 degree angles. The objective of lead synthesis is to convert the monitoring signals from these nonstandard locations to estimates of the standardized Lead I, Lead II, and Lead III difference signals that would be derived from electrodes positioned at the standard right arm (RA), left arm (LA), and left leg (LL) locations and also shown in the figure.

The signals from the nonstandard monitoring locations can be represented by a matrix X containing samples from the monitored electrodes as column vectors. These signals are high pass filtered or processed so that their mean value is zero. In the example set out below, X is an N×2 matrix where N represents the number of samples and two columns are formed from three ECG electrodes.

Since the electrodes need a reference voltage, two independent ECG vectors ($V_n$) may be produced from these three monitoring electrodes ($E_n$).

$$V_1 = E_1 - E_2$$

$$V_2 = E_2 - E_3$$

The third vector may be derived from the other two as follows and is omitted from matrix X to avoid a singular or ill-conditioned system of equations below $$V_3 = V_1 - V_2 = E_1 - E_2 - (E_1 - E_3) = E_1 - E_3$$

The desired standardized signals can be represented by a matrix Y containing each of the output signals as column vectors with the mean removed, for instance an N×3 matrix where columns 1, 2, and 3 represent Leads I, II, and III respectively.

The goal of lead synthesis is to find a transformation matrix C such that $$XC=Y$$

This can also be written in matrix form as follows $$\begin{bmatrix} X_{11} & X_{12} \\ X_{21} & X_{22} \\ X_{31} & X_{32} \\ \vdots & \vdots \\ X_{N1} & X_{N2} \end{bmatrix} \begin{bmatrix} C_{11} & C_{12} & C_{13} \\ C_{21} & C_{22} & C_{23} \end{bmatrix} = \begin{bmatrix} Y_{11} & Y_{12} & Y_{13} \\ Y_{21} & Y_{22} & Y_{23} \\ Y_{31} & Y_{32} & Y_{33} \\ \vdots & \vdots & \vdots \\ Y_{N1} & Y_{N2} & Y_{N3} \end{bmatrix}$$

The squared error between measured ECG vectors Y and estimated ECG vectors $\hat{Y}$ can be calculated as $$\text{error}=\Sigma(Y-\hat{Y})^2$$

The squared error is minimized by calculating C as follows.

$$C=(X^TX)^{-1}X^TY$$

$\hat{Y}$ is the estimate of Y and can be calculated using the following equation.

$$\hat{Y}=XC$$

The optimal transformation matrix C will generally vary from patient to patient and is based on the relative placement of the electrode assembly and the standard three lead electrodes. However, C can be estimated from a database of known ECG signals and used generically. The operator may have the ability to switch between the sampled ECG vectors and the synthesized leads so the most useful view may be selected.

Figure 19:
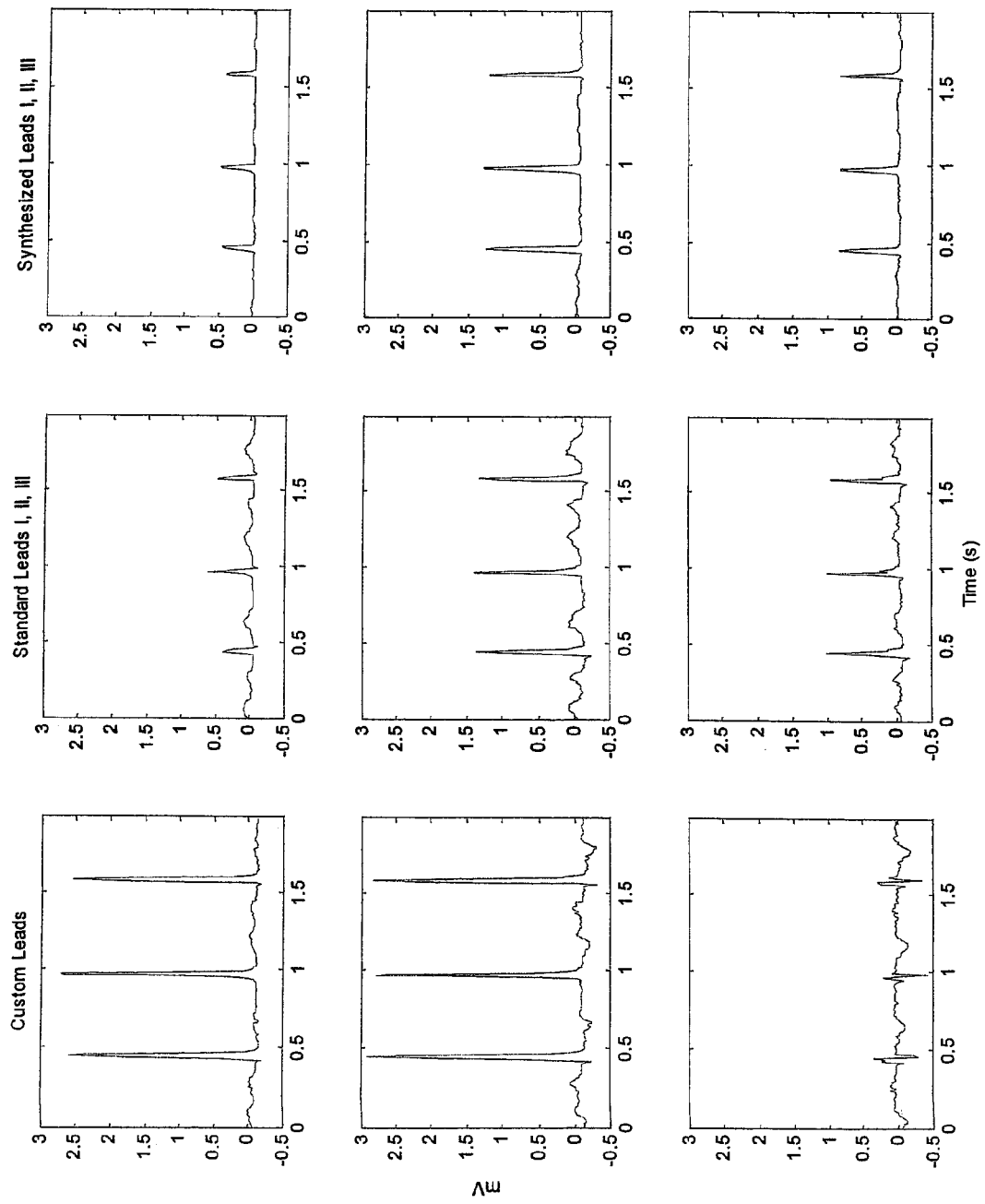
FIG. 19 shows an example of standard monitoring vectors synthesized from nonstandard electrode positions using a matrix transformation.

FIG. 19 illustrates an example of monitoring signals. The signals in the column labeled "Custom Leads" are potential differences measured from a nonstandard electrode configuration such as FIG. 2. The column labeled "Standard Leads I, II, III" are measured by monitoring electrodes such as the ones in FIG. 1. The far right column includes estimates of the standard leads synthesized from the nonstandard signals by a matrix transformation. Although not exactly the same as the signals from standardized locations, they are close enough in appearance for many clinical purposes such as calculation of heart rate.

Electrode Construction

The monitoring and stimulation electrodes may vary in composition. Rather than use a conductive polymer material (sometimes called, "solid gel" or "hydrogel") for both types of electrodes, liquid gel could be used for the monitoring electrodes, and conductive polymer material only for the stimulation electrodes. This has the advantage of better impedance and signal quality shortly after applying the monitoring electrodes to the skin. Conductive polymer pads typically require time for the skin to warm the gel and reduce impedance, whereas liquid gel does not suffer from such delays. Many situations including emergency cardiac pacing or defibrillation are time critical and there may be an advantage to using liquid gels.

It may also be advantageous in some circumstances to use liquid gels (or other conductive agents) for the stimulation electrodes. For instance, a liquid gel may be beneficial if the stimulation electrode is intended for cardiac pacing only.

Other applications may require electrodes (stimulation or monitoring) with a conductive surface(s) but no gel. Conductive gel or electrode paste may be applied to the conductive surface or to the skin as needed. This is generally the preferred method for re-usable ECG or EEG electrodes.

Figure 10:
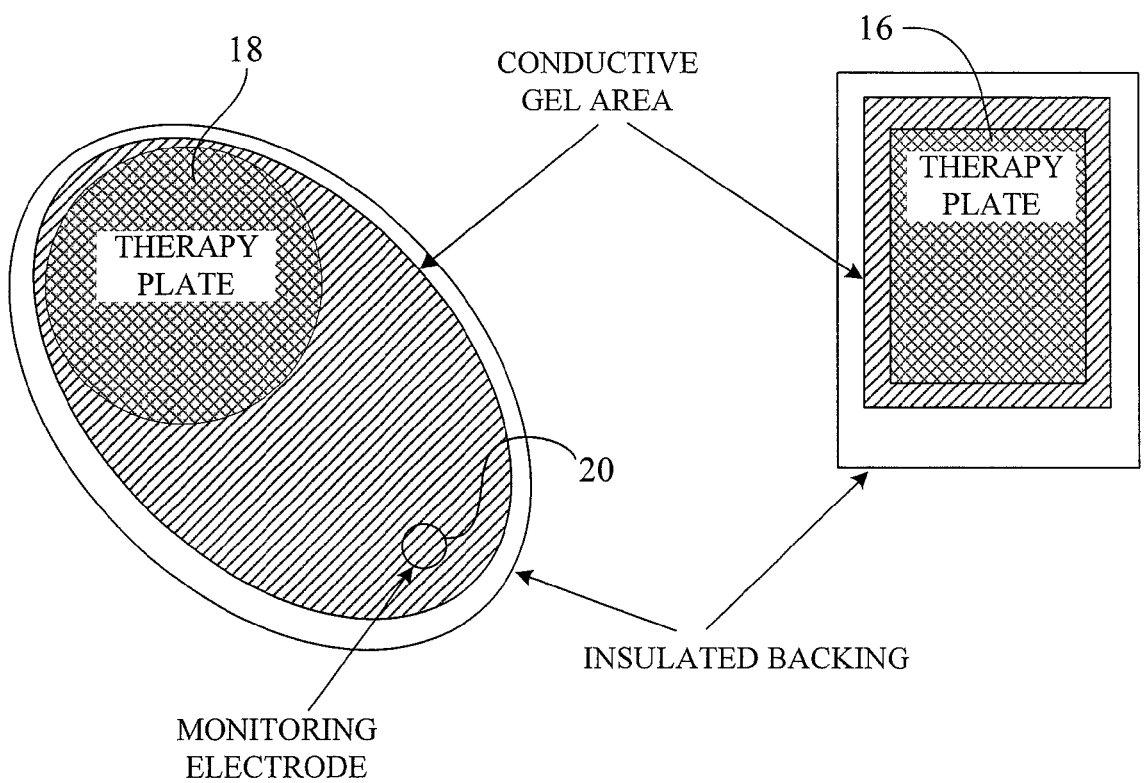
FIG. 10 is a diagrammatic, plan view of an implementation in which a single monitoring electrode is combined with a stimulation electrode.

Electrode assemblies containing more than one electrode (e.g., a stimulation 18 and one or more monitoring electrodes 20) may include multiple conductors (e.g., tin layers) that contact the skin through a common gel (polymer pad or other) layer. FIG. 10 shows such an implementation. Two therapy pad assemblies are used for stimulation. Each pad assembly includes a stimulation electrode, and at least one of the pad assemblies includes one or more monitoring electrodes. Electrical current is driven between the conductive plates of the stimulation electrodes; the plates are in electrical contact with the skin through a conductive gel. During the electrical stimulus a potential difference exists between the plates. The polarization of the plates may persist for some time after the stimulus. Measuring small changes in voltage between the plates of the stimulation electrodes may be difficult because of the relatively large potential differences. But the potential difference between the plate of a stimulation electrode and the plate of an adjacent monitoring electrode is less than the difference between the plates of two stimulation electrodes, and thus monitoring small voltage changes is more feasible. The relative positions of the stimulation and monitoring electrodes may be determined by the measurements of interest, for instance across the heart. If the same conductive gel sheet covers the plates of the stimulation electrode and the plate of the monitoring electrode then the polarization effect will be similar and the differential signal will be less contaminated with artifact.

In some implementations in which the same electrode assembly has more than one type of gel, a vapor barrier may be provided to retard moisture transfer from one gel to another. The electrode assemblies are typically sealed within a package until use, but while this retards moisture from leaving the interior of the sealed package, it does not prevent moisture transfers within the assembly. A lower moisture gel such as a hydrogel may absorb water from a second (e.g. liquid gel or different hydrogel) electrode over the life of the packaged electrode. A vapor barrier inside the package may be used to seal one gel type from the other to increase shelf life. The vapor barrier may be implemented in a variety of ways including the method described by Dupelle and White in U.S. Pat. Nos. 6,453,205 and 6,280,463, in which a sealed cup is used to contain a liquid gel.

The vapor barrier may be made from commonly used materials such as mylar and aluminum. An aluminum thin film layer may be deposited by the so-called thermal evaporation method whereby aluminum wire is evaporated onto a heated crucible in a vacuum chamber. Some implementations may use an inert material that is non conductive, such as a thin film deposition of SiOx (typically via sputter deposition). Other vapor barriers may also be used.

Figure 20:
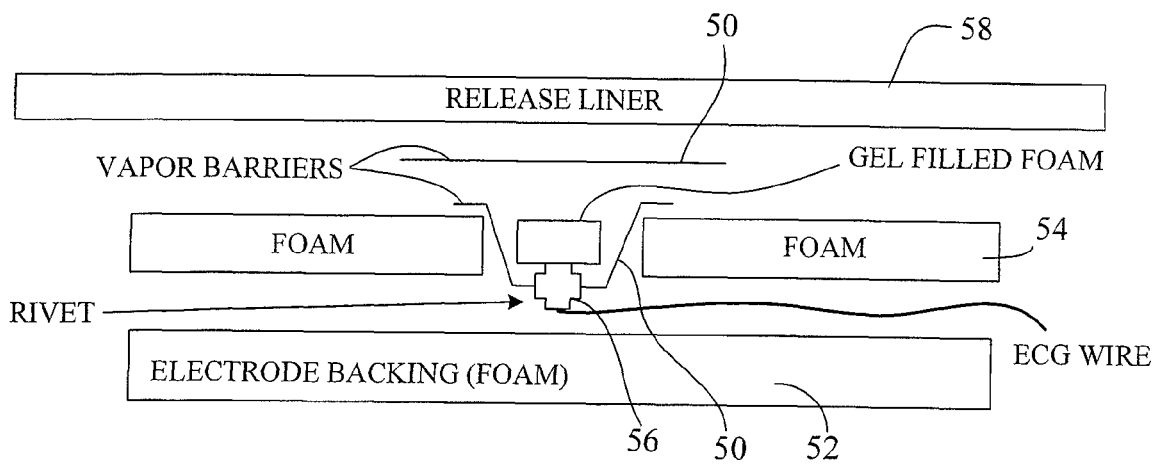
FIG. 20 is a cross-sectional, diagrammatic view of an electrode implementation with an internal vapor barrier.

An exploded cross-sectional view of an electrode with a vapor barrier 50 is shown in FIG. 20 (patient contact surface at top). The outer surface of the electrode is made from a layer of adhesive backed closed cell foam 52 such as Voltek Volara. A second layer of insulating foam 54 creates recessed wells for the monitoring (ECG) electrodes. A thin vapor barrier 50 surrounds the ECG well and adheres to the surrounding foam.

The ECG electrode wire may be riveted (56) through an insulated vapor barrier to maintain the seal. Alternately, the vapor barrier may be a conductive metal such as tin and the wire may be soldered or otherwise connected directly to the vapor barrier.

The entire electrode assembly is placed on a release liner 58 (e.g., silicon impregnated polyethylene). Peeling off the release liner also uncovers the ECG electrodes since the top of the vapor barrier has a stronger bond to the liner than it does to the bottom part of the vapor barrier.

Figure 21:
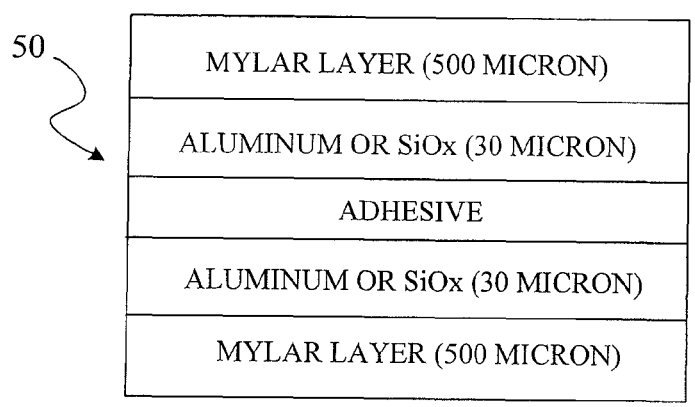
FIG. 21 is a cross-sectional view of the layers of one possible vapor barrier used in the implementation of FIG. 20.

The vapor barrier may be constructed in various ways, but one possibility is shown in FIG. 21, wherein two layers of polyester (e.g., Mylar) and aluminum are bonded face to face.

Electrical Circuitry

Figure 9:
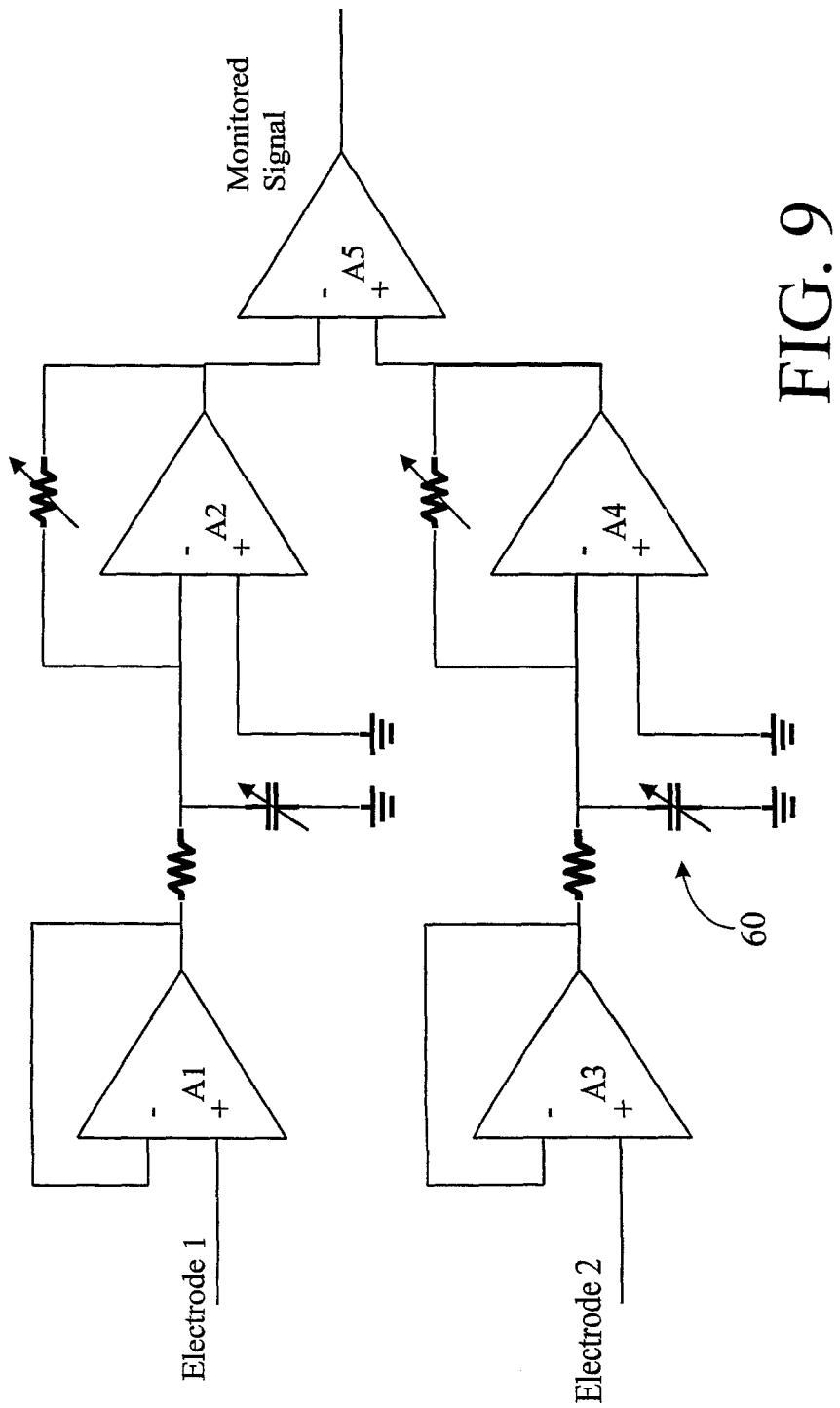
FIG. 9 is an electrical schematic of one implementation for forming the difference between the signal detected on two monitoring electrodes.

FIG. 9 shows one possible analog electrical circuit that can be used to implement artifact rejection. The signal from each of two monitoring electrodes (Electrode 1 and Electrode 2) is buffered through inverting amplifiers A1 and A3, respectively. The buffered signal is fed through a low pass filter, which may be tuned using a variable capacitor to change the time constant. Although a variable capacitor 60 is shown in the circuit, a variable resistor or some other combination of tunable circuit elements may be used. The filters may be set to adjust for different delays in the two input signals so that most of the energy from the artifact will cancel when the signals are subtracted.

FIG. 9 also shows variable gain amplifiers A2 and A4, which allow the signal from each electrode to be scaled so that the magnitude of the artifact is similar in both signals and will cancel when subtracted in the output amplifier A5. With sufficient signal to noise ratio (SNR), only one programmable gain amplifier is needed, provided it can attenuate the signal as well as amplify it.

One example of scaling is an implementation in which two monitoring vectors P1 and P2 are calculated from the signals detected at three electrodes, as follows.

$$P1 = (\text{electrode } 1) - (\text{electrode } 3)$$

$$P2 = (\text{electrode } 2) - (\text{electrode } 3)$$

Then a scaled output Y can be calculated as $$Y = (c1 \times P1) + (c2 \times P2)$$

The constants c1 and c2 may be selected in some implementations so that the magnitude of the artifact in the two monitoring vectors P1, P2 are approximately equal so that the artifact cancels in the scaled output Y. In other implementations, one of the vectors is used without being scaled (so that no constant is necessary).

Figure 22:
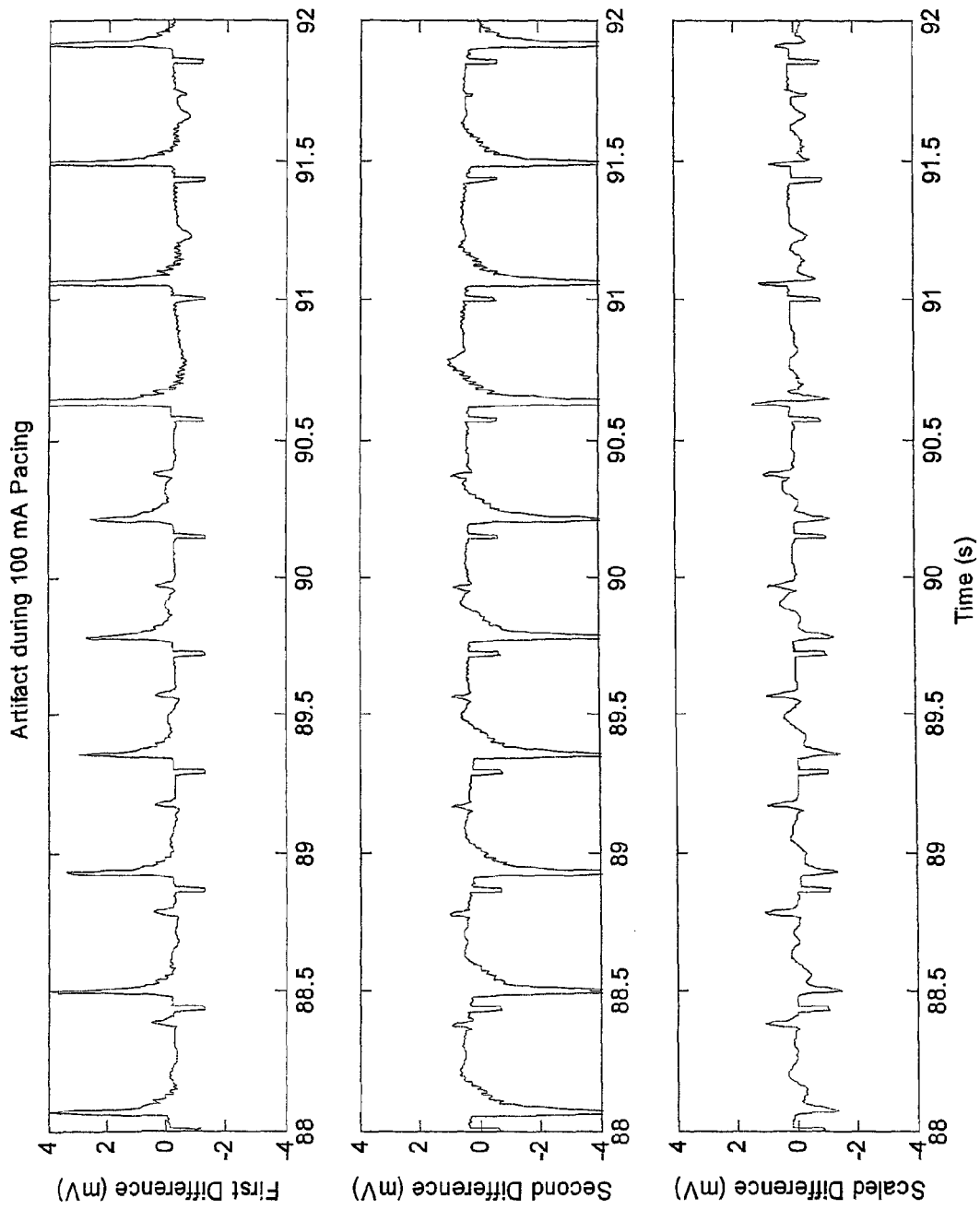
FIG. 22 shows two ECG monitoring signals (upper two signals) and a scaled sum of the signals (lower signal).

FIG. 22 shows an example of how the artifact may be reduced in some implementations with a 100 mA stimulus. The unsealed difference signals (vectors) P1 and P2 (the top two signals) both contain appreciable artifact. But the scaled difference signal (bottom signal) has a substantially reduced artifact, less than in either of the original difference signals. The constants c1 and/or c2 may be derived mathematically by comparing the artifact or may be tuned by the operator (e.g. by twisting a dial) to minimize artifact. The scaling may affect the shape of the resultant monitoring signal (e.g., it may not have magnitudes relevant for diagnostic purposes), but it may be useful for determining heart rate or the general shape of the ECG. The scaling may be implemented in hardware or software, and the constants may be positive or negative depending on the direction of the artifact in each monitored difference signal (vector).

To make it possible for the circuitry to adapt quickly to new patients and new electrodes, some implementations would use digitally controlled components such as (but not limited to) programmable gain amplifiers, digitally controlled variable resistors, and capacitors or inductors that can be switched in or out of the circuit (e.g., with analog switches). Manually adjustable components may also be used, and set by the operator.

The signal processing shown in FIG. 9 may alternatively be implemented using digital or software processing of the sampled signal, or with a combination of analog and digital signal processing. The circuit is preferably designed so that the artifact will not saturate the input amplifiers or converters during periods of interest for monitoring. Digital signal processing may allow for more flexibility in delaying or processing the signals. Digital processing requires sampling the raw signals from each electrode relative to a common reference. Complex filters and/or adaptive gain estimates may also be used in either a digital or analog implementation.

Impedance Adjustment & Common Mode Rejection Circuitry

Another technique for reducing the artifact in the differential signal acquired from two monitoring electrodes is adjusting the input impedance in the electrical circuit that detects the potential at the monitoring electrodes. The artifact will be minimized if the impedance of each monitoring electrode is equal. Electrode impedance can be directly measured or estimated from the artifact. The impedance can be measured by applying a therapy pulse at low or full power, or by using sine waves, chirps, or other arbitrary waveforms suitable for this purpose. The resulting voltage or current waveform measured at each monitoring electrode (or between the two electrodes) can be used to estimate the impedance (or impedance mismatch).

Figure 5:
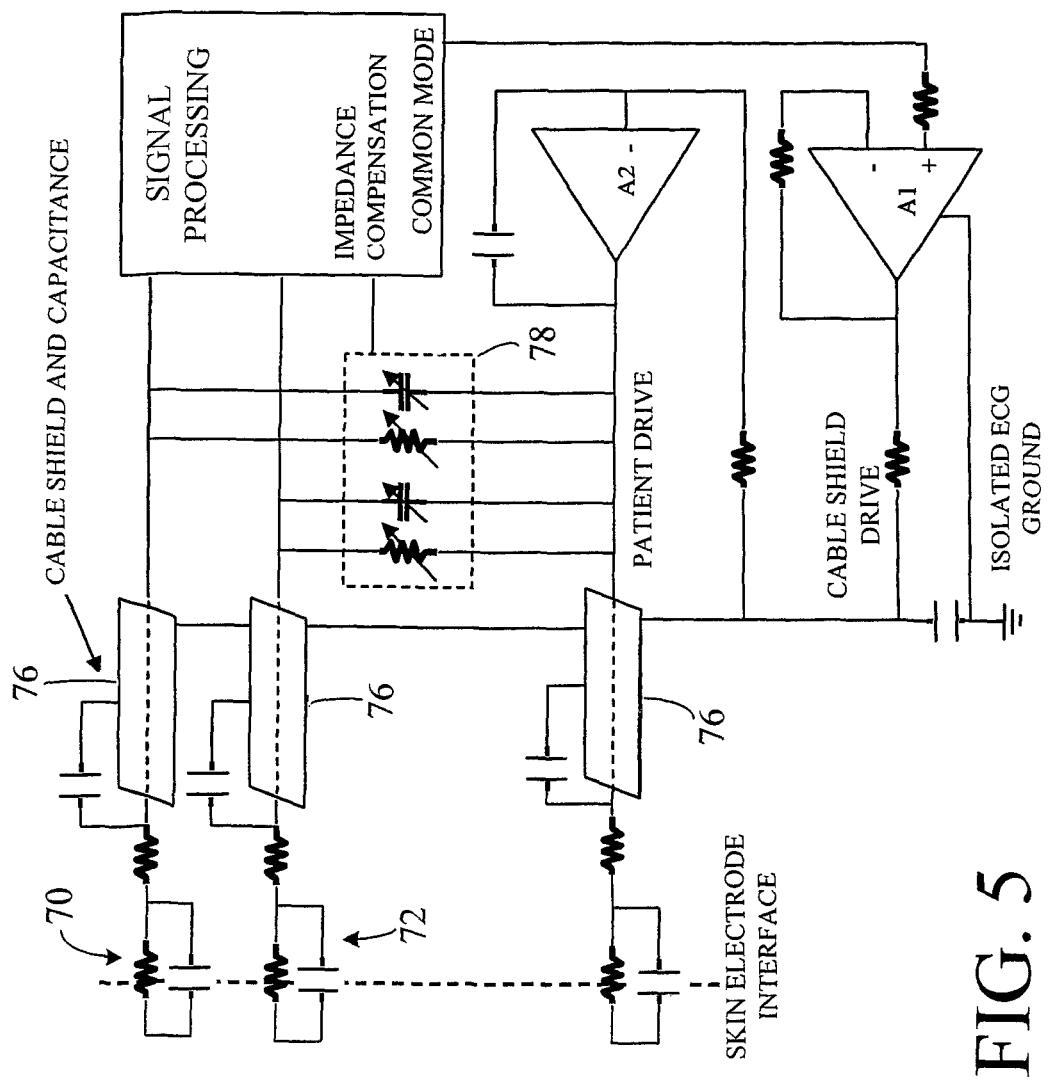
FIG. 5 is an electrical schematic of an implementation in which variable impedances are provided at the inputs of the differential amplifier forming the potential difference between two monitoring electrodes.

One implementation of an impedance balancing circuit is shown in FIG. 5, in which the level of the stimulus artifact at the two electrodes is better equalized, thereby reducing the level of artifact in the differential signal. By balancing the impedance of the monitoring electrodes, it may not be necessary to connect a patient drive electrode to assist in common mode rejection.

The circuit in FIG. 5 shows two monitoring electrodes 70, 72 (upper left) and a patient drive electrode 74 (lower left). Each electrode is shown as an RC element, and it should be noted that these values may vary over time (e.g., from respiration). The conductive gel's contact with the skin may be different at each electrode, resulting in an impedance imbalance between electrodes.

The monitored signal is typically of small magnitude compared to the stimulus artifact and other common mode signals such as power line interference. During or shortly after a stimulation pulse, two monitoring electrodes positioned at the same potential in the electric field between the two stimulation electrodes will measure a very large common mode signal as the result of the polarization on the two stimulation electrodes, i.e., the stimulus artifact. But the circuit measuring the difference between the two monitoring electrodes may not reject the large stimulus artifact if the impedances are not properly balanced.

Several methods are known in the art for canceling common mode signals, and these may be applied to improve cancellation of the stimulus artifact. Each of the leads running to the stimulation and monitoring electrodes has a cable shield 76 surrounding it. The circuit drives the cable shield with the common mode signal through amplifier A1. This reduces the effect of cable capacitance by maintaining signal and shield at similar potentials.

The shield drive is also integrated and inverted by A2 and driven back to the patient. This has the effect of reducing common mode signals by moving the reference level of the circuit close to the common mode of the patient.

Currents due to common mode signals may flow from the patient through various return paths including the patient or shield drive. Circuit elements may be adjusted to correct for imbalances in electrode impedance to reduce common mode signals. The figure shows variable resistors and capacitors controlled by an impedance compensation circuit 78.

The impedance matching circuit may be simpler to implement if placed directly between the two monitoring electrodes, but this may require complex cabling and not be as practical.

Impedance matching elements may include components commonly used in the art, including (but is not limited to) trim pots, manually-adjustable capacitors, digitally-controlled variable resistors or capacitors, or one or more RC elements with analog switches. Inductors or other passive components may also be used.

The impedance compensation controller may include a mix of analog and/or digital processing. The impedance may be measured directly by applying a current to the patient in the form of sine waves, chirps, or therapy pulses at full or reduced intensity. There are other methods well known in the state of the art. It may also be measured indirectly by estimating the imbalance from power line interference or artifact from pulses delivered during therapy. The controller adjusts the digitally controller circuit elements and may monitor changes in common mode artifact. Alternately, the impedance may be adjusted manually by the operator of the device, but this may be time consuming and require some expertise not shared by all device operators.

Cables and Connectors

Various arrangements of cables and connectors can be used for connecting the stimulation (therapy pads) and monitoring electrodes to their associated medical device (e.g., a combined CPR prompting, defibrillation, and pacing device). For example, the therapy electrodes may be wired to a therapy connector. The wires may be made from any electrically conductive material and may be permanently attached to the electrodes or may attach to some or all of the electrodes using a connector. A connector allows the wires to be reused but may be less reliable and takes time for connection. It has the disadvantage of allowing the operator to make a mistake by forgetting to connect a wire or by connecting a wire to the wrong electrode.

The monitoring electrodes may be wired to a monitoring connector. The therapy and monitoring connectors may be physically separate or combined into a unified connector. The unified connector may be one piece or made up of a monitoring connector and therapy connector that can come apart or move in such a way that one or both of the connectors will be attached to the medical device.

This may be accomplished with wires permanently attached to the electrodes and running individually, or attached together in a single cable, to a connector. Attaching the single connector to the medical devices ensures that all connections are properly made. However, this requires a separate input on the medical device for standard leads to be connected, and an internal switching mechanism capable of selecting between electrodes or displaying both sets of leads.

Alternatively, separate connectors may be used for the therapy pad and monitoring electrodes. This has the advantage of allowing the operator to replace one or both of these cables with other monitoring electrodes or pads, and eliminates the need for a switching mechanism. This type of cabling may allow the electrodes to be used on devices not originally designed for this purpose.

Some of the multi-lead cable constructions shown in the application of Peter A. Lund et al., entitled, "Medical Cable", filed on even date herewith (and herein incorporated by reference), may be used in some implementations.

Shared Wires for Therapy and Monitoring Electrodes

To simplify cabling and reduce cost, therapy pad wires may be shared with the monitoring electrodes in certain applications. This is especially relevant where pulses are applied to the therapy pads for short durations, and monitoring is not required during this time. Switching circuitry or non-linear circuit elements including but not limited to, diodes or gas discharge tubes may be used for this purpose.

Figure 8:
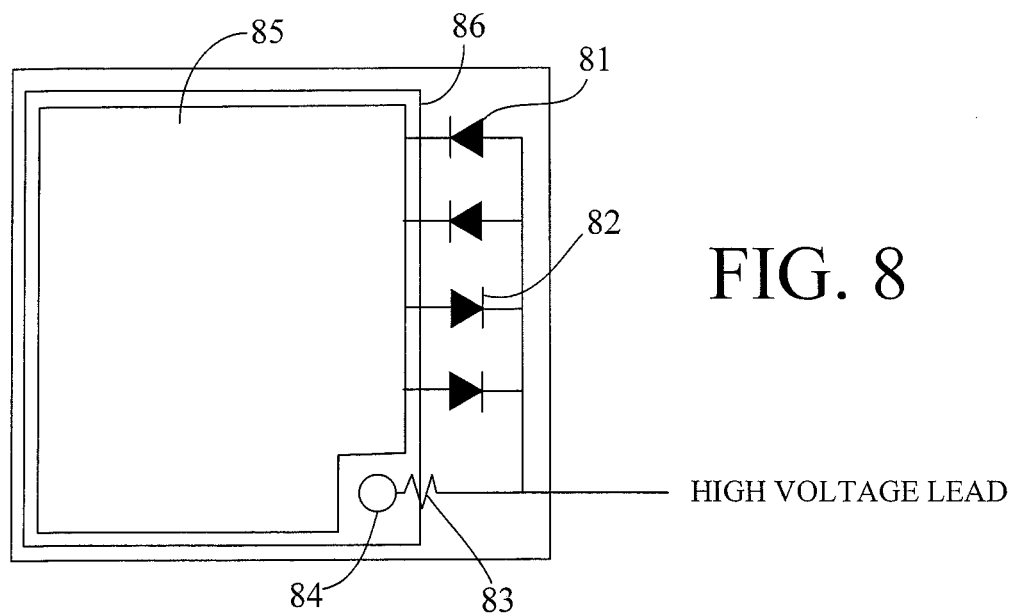
FIG. 8 is a diagrammatic, plan view of an implementation in which diodes are used to reduce the number of electrical leads to the electrode assembly.

A possible implementation of a shared wire electrode assembly is shown in FIG. 8. Diodes 81, 82 allow the flow of current to the stimulation electrode 85 (which conducts to the patient through gel layer 86) but block a reverse flow of current back to the monitoring channel during the monitoring phase following stimulation. Using diodes oriented in both directions allows the delivery of biphasic stimulation waveforms while preventing polarizations (e.g. of less than a diode drop) from being measured by the monitoring circuit. More than one diode may be used in either direction to split high currents or for fault tolerance. Optionally, a resistor 83 or high impedance monitoring electrode 84 may reduce current flow through the monitoring electrode 84 during therapy Implementations such as that of FIG. 8, as well as other shared wire implementations, have the advantages of reduced clutter and reduced chance of wrong connections. In some implementations, the elimination of additional cables may also reduce overall manufacturing cost.

Cancellation with Multiple Stimulating Electrodes

Figure 14:
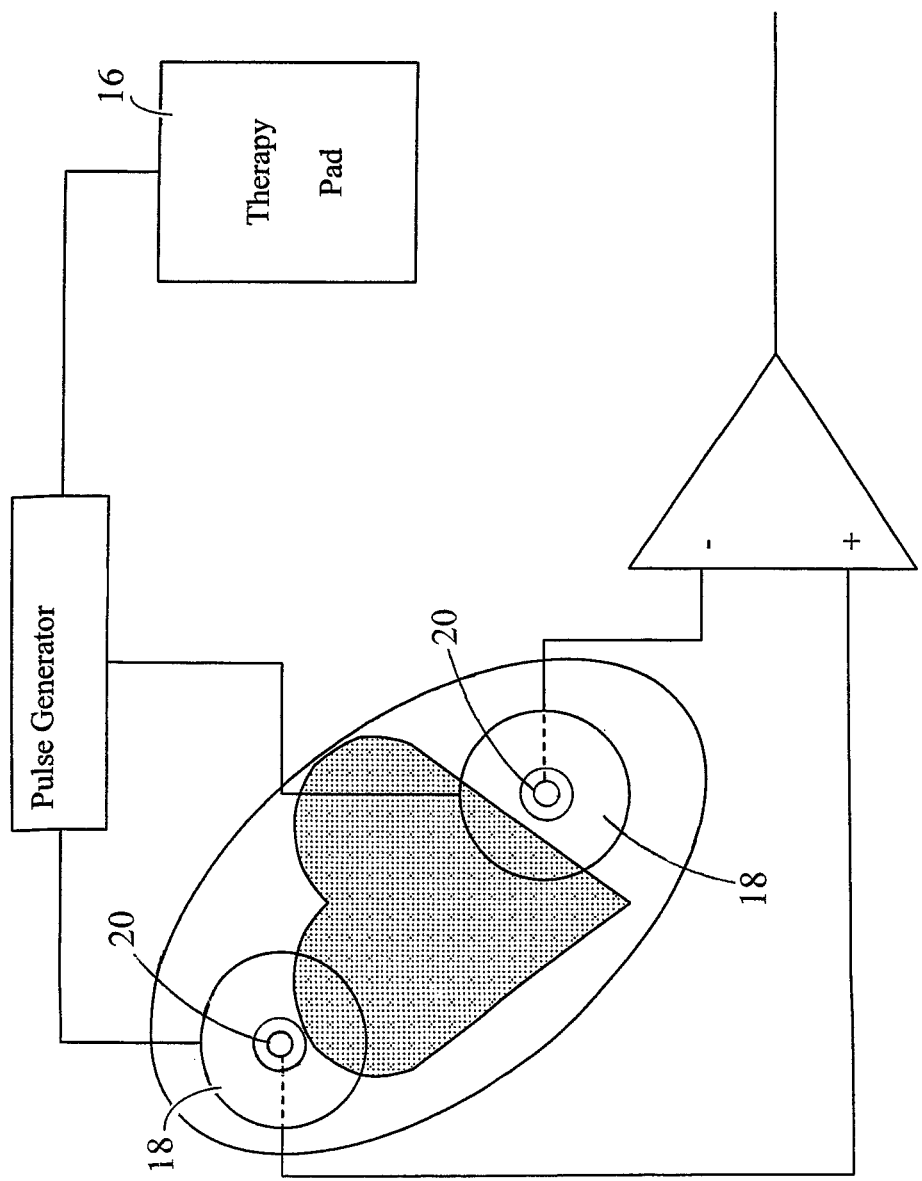
FIG. 14 is a diagrammatic, partially schematic view of an electrode implementation in which a stimulation electrode of one polarity is divided into two smaller stimulation electrodes, and separate monitoring electrodes are positioned at the center of each of the smaller stimulation electrodes.

The configuration shown in FIG. 14 uses a plurality (two shown) of stimulation electrodes 18 of one polarity. Current flows from one positive stimulation electrode 16 to two negative stimulation electrodes 18. In other implementations both the positive and negative stimulation electrodes could be divided into two or more electrodes. A monitoring electrode 20 is positioned in the center (but not in contact with) each negative stimulation electrode. If both of the negative stimulation electrodes are positioned so that each receives (sinks) approximately the same current, the artifact measured by the two monitoring electrodes will be approximately equal and will thus cancel when the difference is taken between the two electrodes.

Figure 12:
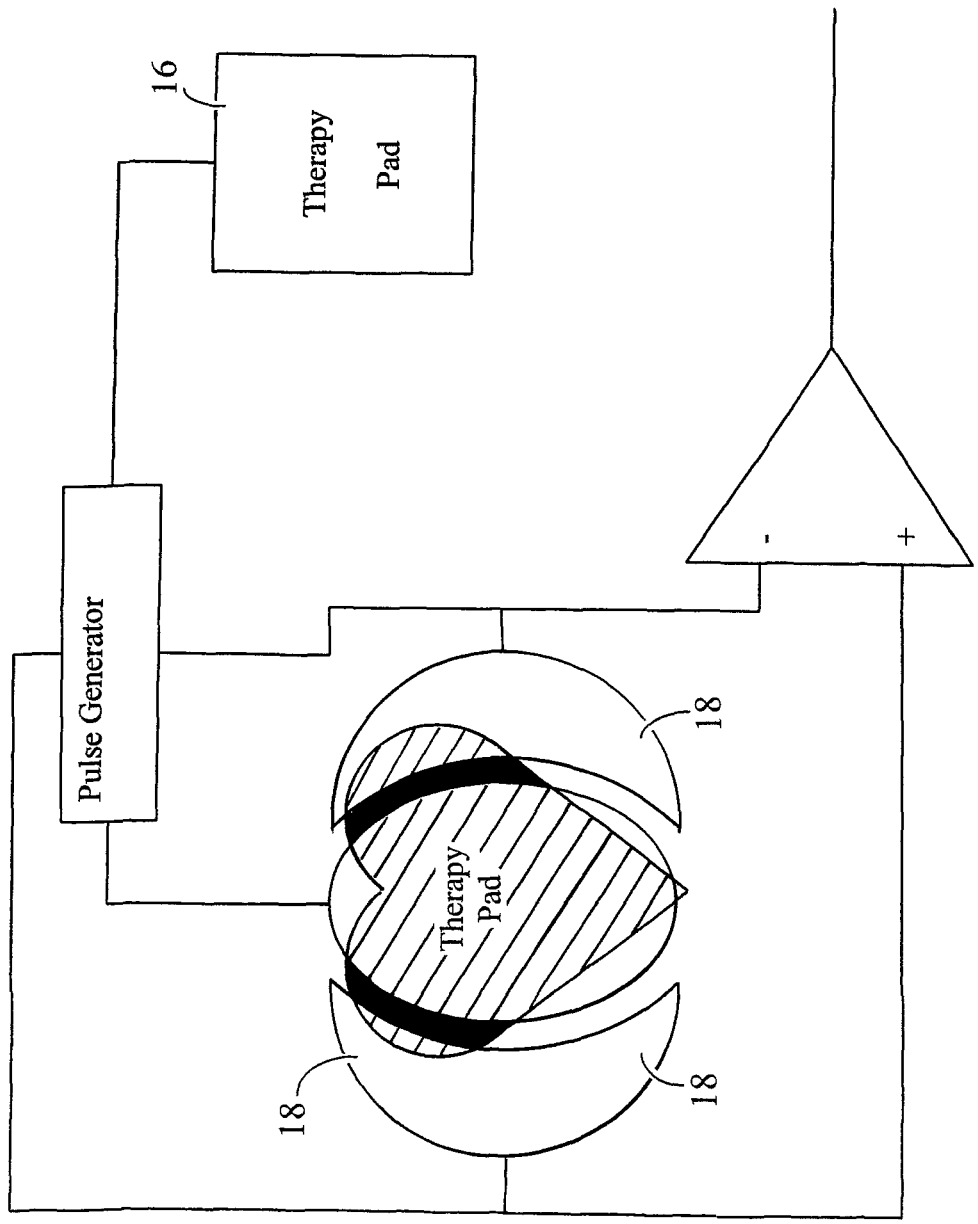
FIG. 12 is a diagrammatic, partially schematic view of an electrode implementation in which a stimulation electrode of one polarity is divided into three smaller electrodes, all three of which may be used for stimulation, and two of which may be used for ECG monitoring.

Another configuration using a plurality of stimulation electrodes 18 of the same polarity is shown in FIG. 12. In this implementation, an electrode of one polarity is divided into three stimulation electrodes 18 (even more separate electrodes could be used), and the other polarity is handled by just a single electrode 16 (but alternatively this polarity could, also, be handled by a plurality of electrodes). The multiple stimulation electrodes of the same polarity have separate conductive plates (e.g., tin), and may have a common conductive gel underlying them, or separate gel areas. All three of the stimulation electrodes are used together during stimulation, and two of the stimulation electrodes are also used for monitoring (as shown by the left and right electrodes leading to the differential amplifier). The two electrodes used for monitoring are positioned across the heart and aligned to produce an ECG vector of interest. These two electrodes may be smaller than the central electrode. Using the two stimulation electrodes for monitoring is possible because the polarization on the two electrodes is approximately equal and of the same polarity. The three electrodes may be part of one assembly, or be split into two or three assemblies for flexibility in placement. The combined area of the three electrodes is made sufficient for the therapy being delivered (e.g., defibrillation or pacing).

Figure 13:
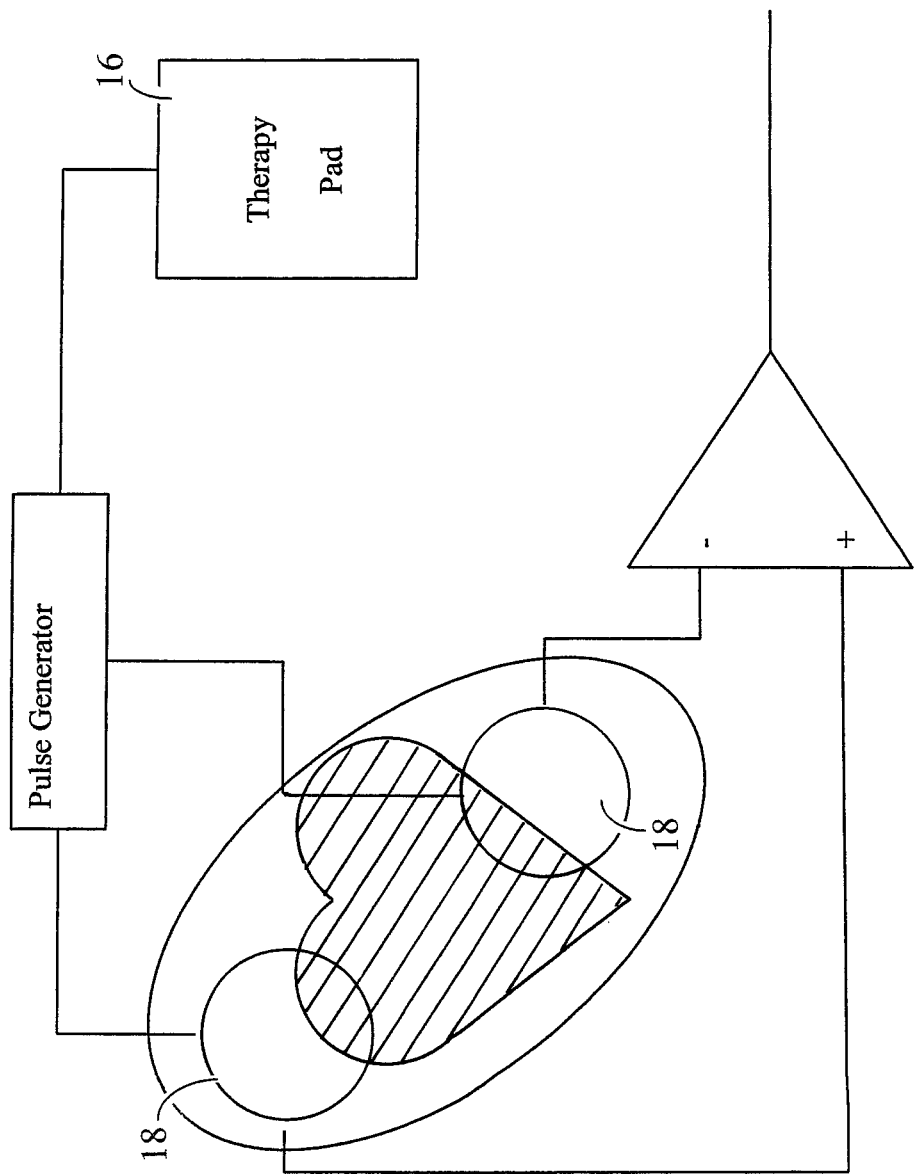
FIG. 13 is a diagrammatic, plan view of an electrode implementation in which a stimulation electrode of one polarity is divided into two smaller stimulation electrodes.

Still another implementation is shown in FIG. 13. Here the central electrode has been eliminated, and one stimulation polarity is divided into two electrodes 18 positioned at two sides of the heart, and aligned to produce an ECG vector of interest. Both electrodes are using during stimulation, and monitoring is done by forming the difference between the two electrodes.

Processing to Further Mitigate Artifact

The stimulus artifact may be mitigated further using analog or digital signal processing. Such processing may include adaptive blanking of the artifact where filter inputs, displays, or strip chart recorders are blanked, zeroed, or otherwise modified during the artifact. An algorithm or adaptive method may be used to adjust the blanking time based on the measured signals. This may allow the operator to view more of the monitored signal if the artifact is cancelled quickly and to prevent confusing artifacts from being displayed if the artifact takes longer to dissipate.

Many other implementations other than those described above are within the invention, which is defined by the following claims.

What is claimed is:

1. A device-implemented method of monitoring and stimulating the exterior of the human body with electrodes, comprising
   delivering stimulation pulses to stimulation electrodes applied to the exterior of the body;
   detecting an electrical potential at monitoring electrodes applied to the exterior of the body,
   positioning at least a first and second monitoring electrode at locations at which an electrical artifact caused by the electrical stimulation pulses is substantially cancelled in a signal formed from the electrical potentials detected at the first and second monitoring electrodes,
   wherein the signal formed from the electrical potentials comprises a difference signal that comprises a difference between the electrical potentials detected at the first and second monitoring electrodes.

2. The method of claim 1 wherein the first and second monitoring electrodes are at locations at which the electrical artifact is substantially equal.

3. The method of claim 1 or 2 wherein the stimulation pulses comprise cardiac stimulation pulses, and the difference signal comprises an ECG signal.

4. The method of claim 3 wherein the cardiac stimulation pulses comprise pacing pulses.

5. The method of claim 4 wherein electrical artifact potential in the ECG difference signal is less than about 10 millivolts measured within 100 milliseconds after termination of the cardiac pacing pulse.

6. The method of claim 4 wherein the electrical artifact potential in the ECG difference signal is less than five times the QRS amplitude when the pacing pulses are of sufficient amplitude to capture the heart.

7. The method of claim 1 wherein there are at least three monitoring electrodes applied to the exterior of the patient, and the first and second monitoring electrodes are selected from among the at least three monitoring electrodes, with the selection being made so as to reduce the effect of the electrical artifact on the difference signal.

8. The method of claim 7 wherein the selection of first and second monitoring electrodes is made automatically by the device rather than manually by the user.

9. The method of claim 8 wherein the automatic selection of the first and second monitoring electrodes varies over time.

10. The method of claim 7 wherein the at least three monitoring electrodes comprise at least two monitoring electrodes positioned at different distances from one of the stimulation electrodes, and wherein the selection of the first monitoring electrode comprises choosing between the two electrodes positioned at different distances.

11. The method of claim 10 wherein the choosing between the two electrodes varies over time.

12. The method of claim 1 further comprising at least a third monitoring electrode applied to the exterior of the patient, and wherein the difference signal comprises the difference between the electrical potential detected at the first electrode and a combination of the electrical potential detected at the second and third electrodes.

13. The method of claim 12 wherein the manner in which the combination is made varies over time to compensate for variation over time of the relative magnitude of the electrical artifact at the second and third electrodes.

14. The method of claim 12 further comprising at least a fourth monitoring electrode applied to the exterior of the patient, and wherein the difference signal comprises the difference between a combination of the electrical potential detected at the first and fourth electrodes and a combination of the electrical potential detected at the second and third electrodes.

15. The method of claim 14 wherein one or both of the combination of the electrical potential detected at the first and fourth electrodes and a combination of the electrical potential detected at the second and third electrodes varies over time.

16. The method of claim 1 wherein the edge-to-edge separation between the active areas of the at least first and second monitoring electrodes and the active area of one of the stimulation electrodes is less than 10 centimeters.

17. The method of claim 1 wherein the at least first and second monitoring electrodes are positioned at the same separation from one of the stimulation electrodes.

18. The method of claim 17 further comprising a third monitoring electrode positioned at the same separation as the first and second electrodes from one of the separation electrodes.

19. The method of claim 17 wherein the first and second monitoring electrodes and the one stimulation electrode are fixed in position on a common substrate.

20. The method of claim 1 wherein the at least first and second monitoring electrodes are positioned so that they are at approximately the same electrical potential in an electric field formed between the two stimulation electrodes when the stimulation electrodes are polarized following a stimulation pulse.

21. The method of claim 1 wherein the at least first and second monitoring electrodes are positioned along approximately the same field line in an electric field formed between the two stimulation electrodes when the stimulation electrodes are polarized following a stimulation pulse.

22. The method of claim 1 wherein the first and second monitoring electrodes are supported on a first substrate that is separate from a second substrate supporting one of the stimulation electrodes.

23. The method of claim 22 wherein the first substrate supporting the first and second monitoring electrodes substantially surrounds the second substrate.

24. The method of claim 23 wherein the first substrate is annular in shape and the second substrate is circular in shape, and the two substrates are positioned approximately concentrically, so that the separation between the two is approximately an equal radial distance.

25. The method of claim 1 wherein the at least first and second monitoring electrodes and the at least one stimulation electrode form one assembly.

26. The method of claim 25 wherein the positions of the at least first and second monitoring electrodes and the stimulation electrode are fixed on the assembly, so that the separation between each of the monitoring electrodes and the stimulation electrode is fixed.

27. The method of claim 1 wherein there are a plurality of difference signals, and the difference signals are used in a transformation to derive ECG signals that resemble standard 3-lead ECG signals.

28. The method of claim 1 wherein the signal is formed in a manner that is varied over time.

29. The method of claim 28 wherein the signal is formed by forming a combination of the electrical potentials at the first end and second monitoring electrodes, and the manner in which the combination is made varies over time.

30. A device-implemented method of monitoring and stimulating the exterior of the human body with electrodes, comprising
    delivering stimulation pulses to stimulation electrodes applied to the exterior of the body;
    detecting an electrical potential at monitoring electrodes applied to the exterior of the body,
    positioning at least a first and second monitoring electrode at locations at which an electrical artifact caused by the electrical stimulation pulses is substantially cancelled in a signal formed from the electrical potentials detected at the first and second monitoring electrodes,
    wherein the detecting an electrical potential at monitoring electrodes comprises an impedance matching circuit to which at least the first and second monitoring electrodes are connected.

31. The method of claim 30 wherein the impedance matching circuit creates an imbalance in the electrode impedances to compensate for variation in the electrical artifact potential in the two monitoring electrodes.

32. A device-implemented method of monitoring and stimulating the exterior of the human body with electrodes, comprising
    delivering stimulation pulses to stimulation electrodes applied to the exterior of the body;
    detecting an electrical potential at monitoring electrodes applied to the exterior of the body,
    positioning at least a first and second monitoring electrode at locations at which an electrical artifact caused by the electrical stimulation pulses is substantially cancelled in a signal formed from the electrical potentials detected at the first and second monitoring electrodes, and
    further comprising having a monitoring device automatically identify a nonstandard monitoring configuration from one or more of the electrodes or from a connector used to the connect the electrodes to the monitoring device, and in the event of identifying the nonstandard monitoring configuration automatically modifying signal processing of the detected electrical potentials.

33. A device-implemented method of monitoring and stimulating the exterior of the human body with electrodes, comprising
    delivering stimulation pulses to stimulation electrodes applied to the exterior of the body;
    detecting an electrical potential at monitoring electrodes applied to the exterior of the body,
    positioning at least a first and second monitoring electrode at locations at which an electrical artifact caused by the electrical stimulation pulses is substantially cancelled in a signal formed from the electrical potentials detected at the first and second monitoring electrodes, and
    further comprising positioning a third electrode on the body, and wherein the signal formed from the electrical potentials comprises a summation of electrical potentials measured at the first and second electrodes with respect to the third electrode, and wherein the electrical artifact is substantially cancelled in the signal as a result of the electrical artifact being of similar magnitude but of opposite polarity in the electrical potentials measured.

34. The method of claim 33 wherein there are at least first and second stimulation electrodes, and the first monitoring electrode is positioned in the vicinity of the first stimulation electrode, and the second monitoring electrode is positioned in the vicinity of the second stimulation electrode.

* * * * *